(12) United States Patent
Demas et al.

(10) Patent No.: US 9,788,763 B1
(45) Date of Patent: Oct. 17, 2017

(54) METHODS FOR MAGNETIC PARTICLE CAPTURE AND SEPARATION

(71) Applicant: Verily Life Sciences LLC, Mountain View, CA (US)

(72) Inventors: Vasiliki Demas, San Jose, CA (US); Vikram Singh Bajaj, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 210 days.

(21) Appl. No.: 14/327,125

(22) Filed: Jul. 9, 2014

(51) Int. Cl.
*A61B 5/00* (2006.01)
*A61B 5/145* (2006.01)
*A61B 5/05* (2006.01)

(52) U.S. Cl.
CPC ............ *A61B 5/145* (2013.01); *A61B 5/0515* (2013.01); *A61B 5/681* (2013.01); *A61B 5/742* (2013.01); *A61B 5/746* (2013.01)

(58) Field of Classification Search
CPC ............ A61B 5/14532; A61B 5/14546; A61B 5/1486; A61B 5/14539; A61B 5/0031; A61B 5/0205; A61B 5/0265; A61B 5/04; A61B 5/04005; A61B 5/04007; A61B 5/04008; A61B 5/0436; A61B 5/05; A61B 5/0515; A61B 5/0522; A61B 5/062; A61B 5/145; A61B 5/681; A61B 5/742; A61B 5/746
See application file for complete search history.

(56) References Cited

U.S. PATENT DOCUMENTS 8,368,396 B2  2/2013  Ueda
8,409,415 B2  4/2013  Liu
8,529,428 B2  9/2013  Creighton
(Continued)

FOREIGN PATENT DOCUMENTS

WO  2013030601 A1  3/2013
WO  2013173235 A1  11/2013

OTHER PUBLICATIONS

Colombo, M., Carregal-Romero, S., Casula, M. F., Gutierrez, L., Morales, M. P., Bohm, I. B., . . . Parak, W. J. (Apr. 5, 2012). Biological Applications of Magnetic Nanoparticles. <http://pubs.rsc.org/en/content/articlepdf/2012/CS/C2CS15337H> Chem. Soc. Rev.,2012,41,4306-4334.*

*Primary Examiner* — Eric Winakur
*Assistant Examiner* — Chu Chuan (JJ) Liu
(74) *Attorney, Agent, or Firm* — McDonnell Boehnen Hulbert & Berghoff LLP

(57) ABSTRACT

Methods of exerting magnetic forces to separate magnetic particles disposed in a portion of subsurface vasculature using a wearable device are provided. The magnetic forces can act to attract, slow, speed, or otherwise influence the magnetic particles in various applications. In some examples, different magnetic forces are exerted on respective sets of magnetic particles to separate the respective sets of magnetic particles. In some examples, similar magnetic forces are exerted on sets of magnetic particles, and separation of the sets of magnetic particles is related to properties of the sets of magnetic particles and/or of the environment of the sets of magnetic particles. In some embodiments, the magnetic particles are configured to bind to an analyte of interest. The separation of the magnetic particles can enable detection of one or more properties of the analyte, modification of the analyte, and/or extraction of the analyte bound to the magnetic particles.

16 Claims, 8 Drawing Sheets

(56) References Cited

U.S. PATENT DOCUMENTS

| | | | |
|---|---|---|---|
| 8,569,044 B2 | 10/2013 | Hoon | |
| 8,624,592 B2 | 1/2014 | Lee | |
| 2004/0073100 A1* | 4/2004 | Ballerstadt | A61B 5/14532 |
| | | | 600/316 |
| 2006/0165805 A1* | 7/2006 | Steinhoff | A61K 48/0075 |
| | | | 424/489 |
| 2009/0024019 A1* | 1/2009 | Stein | G01N 33/54326 |
| | | | 600/409 |
| 2009/0152176 A1* | 6/2009 | Kipp | B03C 1/288 |
| | | | 209/562 |
| 2010/0243574 A1* | 9/2010 | Markov | B03C 1/01 |
| | | | 210/695 |
| 2011/0221427 A1* | 9/2011 | Ovsyanko | G01N 27/745 |
| | | | 324/228 |
| 2012/0135494 A1* | 5/2012 | Murthy | B03C 1/0332 |
| | | | 435/173.9 |
| 2012/0289764 A1 | 11/2012 | Murakami | |
| 2013/0144134 A1* | 6/2013 | Lee | G01N 24/08 |
| | | | 600/309 |
| 2013/0316355 A1 | 11/2013 | Dryga et al. | |
| 2014/0021105 A1* | 1/2014 | Lee | G01N 27/44756 |
| | | | 209/214 |
| 2014/0378794 A1* | 12/2014 | Conrad | A61B 5/681 |
| | | | 600/317 |
| 2015/0213931 A1* | 7/2015 | Kim | H01F 1/0054 |
| | | | 335/296 |

* cited by examiner

METHODS FOR MAGNETIC PARTICLE CAPTURE AND SEPARATION

BACKGROUND

Unless otherwise indicated herein, the materials described in this section are not prior art to the claims in this application and are not admitted to be prior art by inclusion in this section.

A number of scientific methods have been developed to detect, measure, and/or affect one or more analytes in a biological or other environment. The one or more analytes could be any analytes that, when present in or absent from a person's body, or present at a particular concentration or range of concentrations, may be indicative of a medical condition or health state of the person. The one or more analytes could be substances whose distribution, action, or other properties, interactions, or activities throughout an animal's body was of scientific interest. The one or more analytes could be include pharmaceuticals or other substances introduced into the biological or other environment to effect some chemical or biological process. The one or more analytes could be present in living or nonliving human or animal tissue, and could be detected, measured, of affected in an in vivo, ex vivo, in vitro, or some other type of sample. The one or more analytes could include enzymes, reagents, hormones, proteins, drugs, nanoparticles, pharmaceuticals, cells or other molecules.

Detecting, measuring, and/or affecting one or more analytes in a biological or other environment can be accomplished through the use of a contrast agent targeted to and/or part of the one or more analytes. The contrast agent can facilitate detecting, measuring, and/or affecting the one or more analytes by having an optical, magnetic, electromagnetic, acoustical, and/or some other property that is different from (e.g., that contrasts with) the surrounding environment. The contrast between a property of the surrounding environment and the different property of the contrast agent can permit selective manipulation and/or detection of the contrast agent and/or the one or more analytes.

SUMMARY

Some embodiments of the present disclosure provide a method including: (i) positioning a device proximate to an external body surface that is proximate to a portion of subsurface vasculature, wherein the portion of subsurface vasculature contains first magnetic particles and second magnetic particles; and (ii) separating the first and second magnetic particles in the portion of subsurface vasculature, wherein separating the first and second magnetic particles comprises exerting magnetic forces on the first and second magnetic particles, wherein the magnetic forces are exerted by the device.

Some embodiments of the present disclosure present an apparatus, comprising a magnetic field producer, wherein the magnetic field producer is configured to be positioned proximate to an external body surface that is proximate to a portion of subsurface vasculature, wherein the portion of subsurface vasculature contains first magnetic particles and second magnetic particles, wherein the magnetic field producer is configured to separate the first and second magnetic particles in the portion of subsurface vasculature, wherein separating the first and second magnetic particles comprises exerting magnetic forces on the first and second magnetic particles, wherein the magnetic forces are exerted by the magnetic field producer.

These as well as other aspects, advantages, and alternatives, will become apparent to those of ordinary skill in the art by reading the following detailed description, with reference where appropriate to the accompanying drawings.

DETAILED DESCRIPTION

Figure 1A:
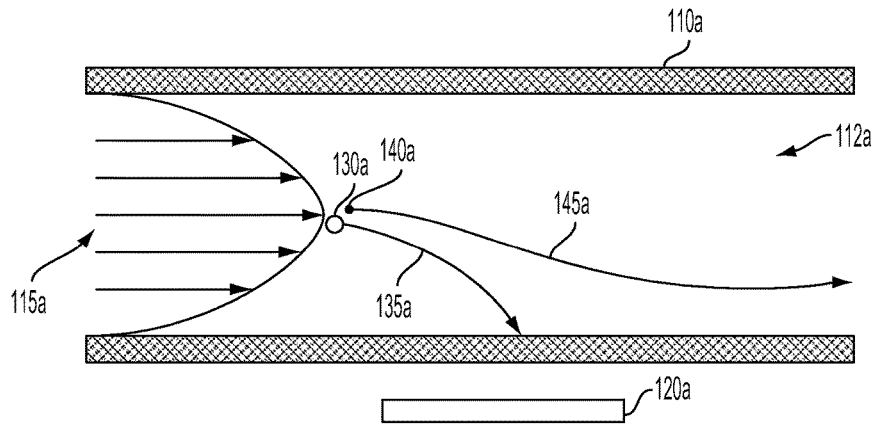
FIG. 1A is cross-sectional view of an example magnetic assembly proximate to magnetic particles in a lumen of subsurface vasculature.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Magnetic particles can be configured to selectively bind with an analyte of interest. Magnetic particles configured in this way can enable manipulation of, detection of, or other interactions with the analytes by applying magnetic forces to the magnetic particles. Additionally or alternatively, an analyte of interest could be intrinsically magnetic, or could be an engineered analyte (e.g., a pharmaceutical) that includes a magnetic property and/or that is bound to a magnetic particle and that can be introduced into an environment according to an application.

Generally, the magnetic particles may be made of and/or wholly or partially coated by an inert material, such as polystyrene, and can have a diameter that is less than about 20 micrometers. In some embodiments, the particles have a diameter on the order of about 10 nm to 1 µm. In further embodiments, small particles on the order of 10-100 nm in diameter may be assembled to form a larger "clusters" or "assemblies on the order of 1-10 micrometers. Those of skill in the art will understand a "particle" in its broadest sense and that it may take the form of any fabricated material, a molecule, cryptophane, a virus, a phage, etc. Further, a particle may be of any shape, for example, spheres, rods, non-symmetrical shapes, etc. In some examples, the particles may be magnetic and can be formed from a paramagnetic, super-paramagnetic or ferromagnetic material or any other material that responds to a magnetic field. Further, the particles can be configured to selectively bind to one or more analytes (e.g., chemicals, hormones, peptides, DNA or RNA fragments, cells).

Separation of two or more types, classes, or other sets of such magnetic particles could enable a variety of applications. The two or more sets of magnetic particles could be configured to selectively interact with (e.g., to bind to) one or more analytes of interest. In some embodiments, separation and/or collection of the two or more sets of magnetic particles could enable to the detection and/or modification of one or more properties of the one or more analytes of interest.

Separation of two or more sets of magnetic particles could be effected by generating a magnetic field having a specified profile in an environment containing the magnetic particles. Properties of the magnetic particles and/or the specified profile could cause differential motions between the two or more sets of magnetic particles related to differences in one or more properties of the two or more sets of magnetic particles, resulting in separation and/or collection of the two or more sets of magnetic particles. In some environments, the magnitude of fluid forces on a magnetic particle (e.g., drag, convection) could be related to the surface and/or cross-sectional area of the magnetic particle and/or other analytes or particles bound to the magnetic particle. The magnitude of a magnetic force exerted on a magnetic particle by a magnetic field could be related to the volume of magnetic material (e.g., the volume of a particle of superparamagnetic iron) in the magnetic particle. Thus, a magnetic field profile (i.e., a pattern of magnitude and direction of a magnetic field) in the environment could be specified to cause separation of magnetic particles related to properties (e.g., sizes, cross-sectional areas, volumes, types of magnetic material, whether the particles are aggregated together and/or bound to an analyte) of the magnetic particles and/or properties of the environment (e.g., a flow profile of fluid in a portion of subsurface vasculature).

Embodiments herein relate to devices that include magnetic field producers (i.e., devices that include one or more permanent magnets, electromagnets, magnetic shims, and/or other magnetic elements and that produce and/or can be operated to produce respective magnetic fields) and that are configured to generate high-strength magnetic fields (i.e., magnetic fields having a high field magnitude and/or field gradient magnitude) having specified profiles such that mounting or otherwise positioning the devices proximate to a portion of subsurface vasculature or other fluid environment causes separation of first and second magnetic particles in the subsurface vasculature or other fluid environment. These embodiments could be applied to manipulate magnetic particles in living (e.g., blood of a living human or animal) or nonliving (e.g., a sample in a container configured to enable imaging or measurement of the sample) biological environments or non-biological environments (e.g., a fluid that is part of a chemical synthesis process). In some embodiments, the devices could be wearable (e.g., configured to be worn around the wrist). Magnetic field producers as described herein could include one or more permanent magnets, electromagnets, high-permeability poles or shims, or other magnetic or partially magnetic elements according to an application.

A magnetic field producer could include one or more permanent magnets. The one or more permanent magnets could be configured to produce high-strength magnetic fields, for example samarium-cobalt magnets, neodymium magnets, rare earth magnets, alnico magnets, ferrites, or other ferromagnetic or otherwise permanently magnetic materials. The one or more permanent magnets could have a variety of orientations (e.g., directions of the magnetic moment of the one or more dipole magnets) relative to a target environment and relative to each other. In some examples, the one or more permanent magnets include three or more dipole magnets arranged as a Halbach array. A magnetic field producer could include one or more electromagnets. A magnetic field producer could be configured to generate a magnetic field having a specified profile in a portion of subsurface vasculature or other region of fluid flow that included a magnetic field gradient in a transverse direction (i.e., substantially parallel to a direction of flow of fluid in the environment, e.g., along the long axis of a pipe or portion of subsurface vasculature) to generate a force on magnetic particles to oppose fluid forces on the magnetic particles due to the flow. Additionally or alternatively, the specified profile could include a magnetic field gradient in a radial direction (i.e., toward the wall(s) of a pipe or portion of subsurface vasculature) to generate a force in magnetic particles to attract the magnetic particles to the wall(s) of the fluid environment containing the magnetic particles. Other specified profiles of a magnetic field in an environment of interest that contains magnetic particles (e.g., a portion of subsurface vasculature) are anticipated.

A variety of differences in properties between first and second magnetic particles could enable separation of the first and second magnetic particles by a magnetic field having a specified profile. In general, these differences can relate to differences in a relationship between the effective cross-sectional and/or surface area of the magnetic particles (i.e., a cross-sectional and/or surface area of the magnetic particle and any other analytes, magnetic particles, or other elements directly or indirectly bound to the magnetic particles) and an effective magnetic moment of the magnetic particles (e.g., a total volume of magnetic material of the magnetic particles and/or any other magnetic particles directly or indirectly bound to the magnetic particles). For example, first magnetic particles could have a first size greater than a second size of second magnetic particles, such that a ratio of magnetic force to fluid dynamic force on the first particles is greater than the ratio for the second particles such that the first particles are collected on a wall of a portion of subsurface vasculature containing the first and second magnetic particles while the second particles are not collected. In another example, a plurality of magnetic particles could be bound to an analyte (i.e., first magnetic particles are aggregates including magnetic particles bound to an analyte, while second magnetic particles are unbound magnetic particles free in the environment) such that a ratio of magnetic force to fluid dynamic force on the analyte/bound magnetic particle aggregates (i.e., the first particles) is greater than the ratio for the unbound magnetic particles (i.e., the second magnetic particles), such that the first particles are collected on a wall of a portion of subsurface vasculature containing the first and second magnetic particles while the second particles are not collected.

Methods, devices, and other embodiments described herein could be configured to enable a variety of applications. In some examples, magnetic particles could be configured to bind to an analyte, such that separation and/or capture of the magnetic particles could enable the detection of one or more properties of the analyte (e.g., a concentration of the analyte). One or more properties of the analyte could be related to a medical condition of a human or animal containing the analyte. In some examples, the analyte could have a medical or other effect on the human or animal (e.g., the analyte is a toxin, the analyte is a pharmaceutical, the analyte is a cancer cell), and separating and/or collecting magnetic particles bound to the analyte could modulate or otherwise affect a medical condition of the human or animal. In some examples, separation and or collection of the magnetic particles could enable collection of the analyte for analysis outside the body of the human or animal. Other applications and environments containing magnetic particles are anticipated.

It should be understood that the above embodiments, and other embodiments described herein, are provided for explanatory purposes, and are not intended to be limiting.

Further, the term "medical condition" as used herein should be understood broadly to include any disease, illness, disorder, injury, condition or impairment—e.g., physiologic, psychological, cardiac, vascular, orthopedic, visual, speech, or hearing—or any situation requiring medical attention.

II. Illustrative Magnetic Particles and Separation Thereof

In some examples, magnetic forces are exerted on magnetic particles disposed in a fluid environment to separate two or more of the magnetic particles. The fluid environment could include artificial environments (e.g., a fluid of an industrial process, a fluid of a chemical or pharmaceutical process) and natural environments (e.g., a lake, a river, a marsh, blood in vasculature of an animal). For example, the magnetic particles could be disposed in blood in a portion of subsurface vasculature of a human. The magnetic particles could be permanently magnetized (e.g., could be ferromagnetic) or could become magnetized when exposed to a magnetic field (e.g., could be paramagnetic) or to some other factor. Exerting a magnetic force on such magnetic particles could include providing a magnetic field in the environment of the magnetic particles having a high magnitude of magnetic field gradient, such that permanent and/or induced magnetic moments of the magnetic particles are attracted in the direction of (i.e., experience an exerted magnetic force in the direction of) the gradient. Exerting a magnetic force on such magnetic particles could additionally or alternatively include providing a magnetic field in the environment of the magnetic particles having a high magnitude, such that magnetic moments are induced in the magnetic particles and/or permanent and/or induced magnetic moments of the magnetic particles experience a torque aligning the magnetic moments with the direction of the magnetic field.

Generally, the magnitude of a magnetic force exerted on a magnetic particle is related to the magnitude of the permanent and/or induced magnetic dipole moment of the magnetic particle. In some examples, the magnitude of the permanent and/or induced magnetic dipole moment can be related to the mass and/or volume of magnetic material included in the magnetic particle. For example, the magnitude of the induced magnetic dipole moment of a magnetic particle that includes a particle of superparamagnetic iron oxide could be related to the volume of the particle of superparamagnetic iron oxide. The magnetic particles could be artificial (e.g., functionalized polystyrene shells containing and/or coating particles of superparamagnetic iron oxide), natural (e.g., particles of magnetite encapsulated in lipid bilayers in a cell), or could contain natural and artificial elements (e.g., an artificial magnetic particle onto which a variety of natural antibodies are adsorbed or otherwise attached).

Generally, the magnetic particles may be made of and/or wholly or partially coated by an inert material, such as polystyrene, and can have a diameter that is less than about 20 micrometers. In some embodiments, the magnetic particles have a diameter on the order of about 10 nm to 1 μm. In further embodiments, small particles on the order of 10-100 nm in diameter may be assembled to form larger "clusters" or "assemblies" on the order of 1-10 micrometers. Those of skill in the art will understand a "particle" in its broadest sense and that it may take the form of any fabricated material, a molecule, tryptophan, a virus, a phage, etc. Further, a magnetic particle may be of any shape, for example, spheres, rods, non-symmetrical shapes, etc. In some examples, a magnetic material of the magnetic particles can include a paramagnetic, super-paramagnetic or ferromagnetic material or any other material that responds to a magnetic field. In some examples, the magnetic particles can include a magnetic moiety. Further, the particles can be configured to selectively bind to one or more analytes (e.g., chemicals, hormones, peptides, DNA or RNA fragments, cells). In some examples, the magnetic particles could be considered to include other elements (e.g., analytes, other magnetic or non-magnetic particles) bound to the magnetic particles. For example, a 'first magnetic particle' could include a particle of magnetic material functionalized to selectively interact with an analyte, and a 'second magnetic particle' could include one or more of the 'first magnetic particles' bound to the analyte, such that the 'second magnetic particle' is a composite particle including at least one instance of the analyte. Other embodiments of magnetic particles are anticipated.

In some examples, the magnetic particles are functionalized to selectively interact with an analyte of interest. The magnetic particles can be functionalized by covalently attaching a bioreceptor designed to selectively bind or otherwise recognize a particular analyte (e.g., a clinically-relevant analyte, e.g., a cancer cell). For example, magnetic particles may be functionalized with a variety of bioreceptors, including antibodies, nucleic acids (DNA, siRNA), low molecular weight ligands (folic acid, thiamine, dimercaptosuccinic acid), peptides (RGD, LHRD, antigenic peptides, internalization peptides), proteins (BSA, transferrin, antibodies, lectins, cytokines, fibrinogen, thrombin), polysaccharides (hyaluronic acid, chitosan, dextran, oligosaccharides, heparin), polyunsaturated fatty acids (palmitic acid, phospholipids), or plasmids. The functionalized magnetic particles can be introduced into a portion of subsurface vasculature of a person by injection, ingestion, inhalation, transdermal application, or in some other manner. In some examples, two or more types of magnetic particles could be configured to selectively interact with respective two or more analytes of interest. For example, first magnetic particles could be configured to selectively interact with a first analyte of interest and second magnetic particles could be configured to selectively interact with a second analyte of interest. Separation, collection, or other manipulations of the first and second magnetic particles by exerting magnetic forces on the first and second magnetic particles could enable a variety of applications related to the first and second analytes of interest.

A clinically-relevant analyte could be any substance that, when present in the blood of a person or animal, or present at a particular concentration or range of concentrations, may be indicative and/or causative of an adverse medical condition. For example, the clinically-relevant analyte could be an enzyme, hormone, protein, other molecule, or even whole or partial cells. In one relevant example, certain proteins have been implicated as a partial cause of Parkinson's disease. Thus, the development of Parkinson's disease might be prevented or retarded by providing magnetic particles functionalized with a bioreceptor that will selectively bind to this target. A magnetic force may then be exerted on these bound magnetic particles, using one or more magnetic assemblies as described herein (e.g., a magnetic assembly in a wearable device mounted to an external body surface proximate to a portion of subsurface vasculature), to collect, separate, detect, modify, or otherwise interact with the bound protein. As a further example, the analyte could be a cancer cell. By selectively collecting and then detecting, extracting (e.g., by use of an intravenous syringe), modifying, or destroying individual cancer cells (e.g., by emitting energy toward the magnetic particles such that the magnetic particles are heated sufficiently to cause an increase in temperature of the proximate bound cancer cells), the spread of cancer may be diminished and/or quantified.

Magnetic particles and/or magnetic assemblies configured to exert magnetic forces on such magnetic particles (and devices including such magnetic assemblies) could be configured and/or operated to provide a number of different applications. Applications could include detecting one or more properties of the magnetic particles, one or more properties of an analyte bound to or otherwise selectively interacting with the magnetic particles, collecting and/or extracting the magnetic particles and/or analytes bound to the magnetic particles, modifying and/or destroying the magnetic particles and/or analytes bound to the magnetic particles, or other applications.

Separation of first and second magnetic particles could include exerting a variety of magnetic forces in a variety of environments to effect a variety of changes in the location, velocity or other properties of the first and second magnetic particles. Generally, separation of first and second magnetic particles includes causing and/or changing a change in relative displacement, velocity, and/or acceleration between the first and second magnetic particles such that a region experiences a relative increase in an amount of the first magnetic particles contained in the region and/or a relative decrease in an amount of the second magnetic particles contained in the region. For example, a magnetic force could be exerted on the first and second magnetic particles such that the first magnetic particles are collected in a region while the second magnetic particles are not attracted and/or are repelled from the region. In some examples, magnetic forces could be applied to first and second magnetic particles in a region such that the first and second magnetic particles exhibited a relative displacement away from each other. For example, the first and second magnetic particles could be carried in a flow through a region, and a magnetic force could be exerted such that the velocity of the first magnetic particles in the region is retarded such that the concentration of the first magnetic particles in the region is increased. In another example, the first magnetic particles could experience a force causing a displacement of the first magnetic particles toward a first sub-region (e.g., a medial wall of a vein) and the second magnetic particles could experience a force causing a displacement of the second magnetic particles toward a second sub-region (e.g., a lateral wall of a vein). Other examples of separation of first and second magnetic particles and/or of additional magnetic particles are anticipated.

In some examples, a magnetic assembly could be configured to exert a first magnetic force on first magnetic particles and to exert a second magnetic force on second magnetic particles such that the difference between the first and second magnetic forces is sufficient to cause separation of the first and second magnetic particles. For example, the first magnetic particles could have a first magnetic moment (e.g., related to a first characteristic size of the first magnetic particles) and the second magnetic particles could have a second magnetic moment (e.g., related to a second characteristic size of the second magnetic particles) that is different from the first magnetic moment.

Additionally or alternatively, the magnetic force exerted on the magnetic particles could be substantially the same between different sets of magnetic particles (e.g., between first and second magnetic particles), but some other force (e.g., fluid drag) could be different between first and second magnetic particles such that exerting the magnetic force causes separation of the first and second magnetic particles.

In some examples, magnetic particles could be configured to bind to an analyte of interest, and a magnetic assembly could be configured to collect or otherwise manipulate the magnetic particles to enable the detection, extraction, modification, or other manipulation of the analyte. For example, the magnetic assembly could be configured to produce a magnetic field in the portion of subsurface vasculature such that first magnetic particles (i.e., aggregate particles comprising instances of an analyte and magnetic particles bound thereto) experience a greater magnetic force than second magnetic particles (i.e., unbound instances of the magnetic particles) such that the first and second magnetic particles can be separated.

Separation of first and second magnetic particles could be due additionally or alternatively to other differences between the properties of and/or environment of the first and second magnetic particles. Magnetic particles could experience a state change related to the environment (e.g., pH, temperature, presence of one or more analytes and/or other chemical or biological elements, a radiation level, an intensity, wavelength, polarization, or other property of illumination in the environment) of the magnetic particles and/or a state of the magnetic particles (e.g., a spin state, an excited energy state, a binding state, a protein folding state, a conformation, an orientation, a phosphorylation state, a methylation state, the presence of a sandwich assay protein to the magnetic particles). A magnetic assembly could be configured to produce a specified magnetic field profile (i.e., to produce a magnetic field having one or more specified properties, e.g., field intensity, field gradient intensity, field gradient direction at one or more locations in a region of interest containing magnetic particles) that is related to the properties of the first and second magnetic particles and/or the environments of the first and second magnetic particles to effect separation, collection, or some other manipulation of the first and second magnetic particles.

In some applications, separation and/or manipulation of magnetic particles could enable detection and/or modification of an analyte. For example, the reaction (e.g., a differential and/or absolute motion) of a magnetic particle to a magnetic field generated by a magnetic assembly could be detected, and one or more properties of the reaction could be used to determine one or more properties of the magnetic particle. For example, a change in velocity of a magnetic particle, when exposed to the magnetic field of the magnetic assembly, could be related to whether the magnetic particle was bound to an analyte. In some examples, the magnetic particles could be configured to couple an oscillating electromagnetic field into an increase in heat proximate to the magnetic particle, and this increase in heat could be used to detect one or more properties of the magnetic particle and/or to modify the environment proximate to the particle (e.g., to denature an analyte bound to the magnetic particle). Other configurations, operations, and applications of the embodiments described herein are anticipated.

In some embodiments, a detector could be disposed proximate to a magnetic assembly that is configured to separate the magnetic particles, and the detector could detect one or more properties of an analyte bound to some or all of the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the separated and/or collected magnetic particles sufficient to alter one or more properties of the analyte (e.g., to destroy, denature, heat, change a conformation state of, other otherwise modify the analyte). In some examples, separation and collection of an analyte bound to magnetic particles by a magnetic assembly could enable the extraction of the analyte and magnetic particles (e.g., using a hypodermic needle).

Exerting a force on magnetic particles could include exerting an attractive magnetic force on the magnetic particles. That is, a magnetic assembly could be configured to attract the magnetic particles toward the magnetic assembly. In some examples, the magnetic assembly could be configured to exert an attractive magnetic force of sufficient magnitude to collect the magnetic particles proximate to the magnetic assembly. For example, the magnetic particles could be disposed in blood of a wearer of a wearable device that includes the magnetic assembly, and the wearable device including the magnetic assembly could be mounted to an external body surface of the wearer proximate to the portion of subsurface vasculature such that the magnetic particles collect in the portion of subsurface vasculature proximate to the magnetic assembly.

In some examples, the magnetic or other differences in properties between first and second sets of magnetic particles could be intrinsic to individual instances of the first and second magnetic particles. For example, the first magnetic particles could have a first magnetic moment, coefficient of drag, cross-sectional area, or some other property, and the second magnetic particles could have a second magnetic moment, coefficient of drag, cross-sectional area, or some other property such that the first and second magnetic particles can be separated by a magnetic assembly.

FIG. 1A illustrates a lumen 112a of a blood vessel (i.e., a portion of subsurface vasculature) 110a. Blood in the lumen 112a is flowing, and the flow of the blood within the blood vessel 110a has a flow profile 115a related to location within the blood vessel 110a; i.e., blood flows faster in the middle of the blood vessel 110a and slower toward the edges. A first magnetic particle 130a and a second magnetic particle 140a are located in the middle of the lumen 112a of the blood vessel 110a. A magnetic assembly 120a (e.g., a device including permanent magnets, magnetic shims, electromagnets, and/or other magnetic components) is disposed outside of the blood vessel 110a (e.g., part of a device positioned proximate to an external body surface proximate to the blood vessel 110a) and is configured to exert a magnetic force on the first 130a and second 140a magnetic particles.

The first 130a and second 140a magnetic particles have one or more properties (e.g., a characteristic size, a magnetic moment, a cross-sectional area, a drag coefficient, a state of binding and/or aggregation with one or more other particles or elements) that are different such that the magnetic assembly 120a exerting magnetic forces on the first magnetic particle 130a and the second magnetic particle 140a causes the first magnetic particle 130a to be collected near the wall of the blood vessel 110a proximate to the magnetic assembly 120a (illustrated by the first path 135a of the first magnetic particle 130a). The second magnetic particle 140a flows away from the magnetic assembly 120a and out of the illustration portion of the blood vessel 110a (illustrated by the second path 145a of the second magnetic particle 140a).

The magnetic force exerted by the magnetic assembly 120a on the first 130a and second 140a magnetic particles includes a force toward the wall of the blood vessel 110a to attract and/or collect the first magnetic particle 130a. The magnetic force could additionally include a force parallel to the direction of the flow of blood in the blood vessel 110a, e.g., to slow the velocity of the first magnetic particle 130a such that the first magnetic particle 130a could be collected.

In some examples, the magnetic or other differences in properties between first and second sets of magnetic particles could be related to the environment of the first and second magnetic particles. For example, the first magnetic particles could be aggregate particles consisting of multiple instances of second magnetic particles and/or other elements (e.g., multiple instances of the second magnetic particles bound to a cell or other analyte). For example, blood within the portion of subsurface vasculature containing the magnetic particles could exhibit a flow profile, and the first magnetic particles could be located in a low-flow region of the flow profile and the second magnetic particles could be located in a high-flow region of the flow profile such that the magnetic forces exerted by the magnetic assembly cause separation of the first and second magnetic particles. Thus, the separation could involve collection of the first magnetic particles in the portion of subsurface vasculature, while the second magnetic particles flow away from the portion of subsurface vasculature.

Figure 1B:
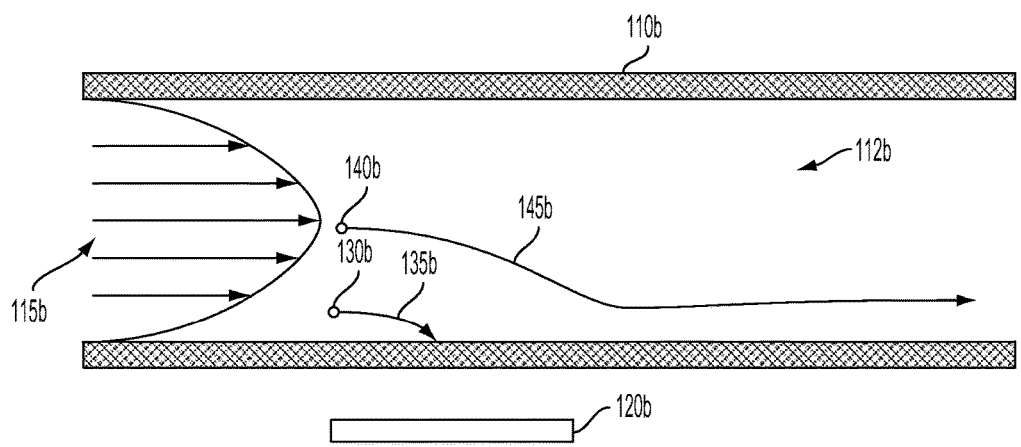
FIG. 1B is cross-sectional view of an example magnetic assembly proximate to magnetic particles in a lumen of subsurface vasculature.

FIG. 1B illustrates a lumen 112b of a blood vessel (i.e., a portion of subsurface vasculature) 110b. Blood in the lumen 112b is flowing, and the flow of the blood within the blood vessel 110b has a flow profile 115b related to location within the blood vessel 110b; i.e., blood flows faster in the middle of the blood vessel 110b and slower toward the edges. A first magnetic particle 130b and a second magnetic particle 140b are located at different locations in the lumen 112b of the blood vessel 110b (i.e., the second magnetic particle 140b is in a high-flow region in the middle of the lumen 112b of the blood vessel 110b and the first magnetic particle 130b is in a lower-flow region at the edge of the lumen 112b of the blood vessel 110b). A magnetic assembly 120b (e.g., a device including permanent magnets, magnetic shims, electromagnets, and/or other magnetic components) is disposed outside of the blood vessel 110b (e.g., part of a device positioned proximate to an external body surface proximate to the blood vessel 110b) and is configured to exert a magnetic force on the first 130b and second 140b magnetic particles.

The first 130b and second 140b magnetic particles have one or more properties (e.g., a characteristic size, a magnetic moment, a cross-sectional area, a drag coefficient, a state of binding and/or aggregation with one or more other particles or elements) that are substantially the same. Conversely, one or more properties of the respective environments of the first 130b and second 140b magnetic particles (e.g., a magnetic field intensity, a magnetic field gradient intensity, a magnetic field gradient direction, a fluid flow rate, a fluid viscosity, a fluid turbulence) are different such that the magnetic assembly 120b exerting magnetic forces on the first magnetic particle 130b and the second magnetic particle 140b causes the first magnetic particle 130b to be collected near the wall of the blood vessel 110b proximate to the magnetic assembly 120b (illustrated by the first path 135b of the first magnetic particle 130b). The second magnetic particle 140b flows away from the magnetic assembly 120b and out of the illustrated portion of the blood vessel 110b (illustrated by the second path 145b of the second magnetic particle 140b).

The magnetic force exerted by the magnetic assembly 120b on the first 130b and second 140b magnetic particles includes a force toward the wall of the blood vessel 110b to attract and/or collect the first magnetic particle 130b. The magnetic force could additionally include a force parallel to the direction of the flow of blood in the blood vessel 110b, e.g., to slow the velocity of the first magnetic particle 130b such that the first magnetic particle 130B could be collected.

Figure 1C:
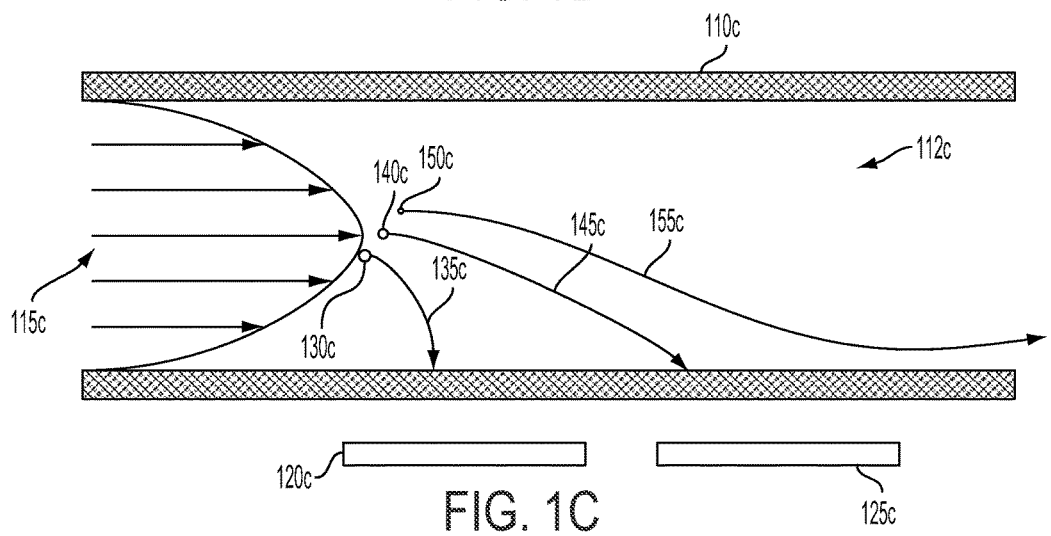
FIG. 1C is cross-sectional view of an example magnetic assembly proximate to magnetic particles in a lumen of subsurface vasculature.

In some examples, a magnetic assembly or other magnetic device could include multiple separation and/or collection stages to implement more complicated separation and/or to separate, collect, and/or otherwise magnetically manipulate more than two sets of magnetic particles. FIG. 1C illustrates a lumen 112c of a blood vessel (i.e., a portion of subsurface vasculature) 110c. Blood in the lumen 112c is flowing, and the flow of the blood within the blood vessel 110c has a flow profile 115c related to location within the blood vessel 110c; i.e., blood flows faster in the middle of the blood vessel 110c and slower toward the edges. A first magnetic particle 130c, a second magnetic particle 140c, and a third magnetic particle 150c are located in the middle of the lumen 112c of the blood vessel 110c. A magnetic device including a first magnetic assembly 120c (e.g., a device including permanent magnets, magnetic shims, electromagnets, and/or other magnetic components) and a second magnetic assembly 125c is disposed outside of the blood vessel 110c (e.g., part of a device positioned proximate to an external body surface proximate to the blood vessel 110c) and is configured to exert a magnetic force on the first 130c, second 140c, and third 150c magnetic particles.

The first 130c, second 140c, and third 150c magnetic particles have one or more properties (e.g., a characteristic size, a magnetic moment, a cross-sectional area, a drag coefficient, a state of binding and/or aggregation with one or more other particles or elements) that are different such that the first magnetic assembly 120c exerting magnetic forces on the first 130c, second 140c, and third 150c magnetic particles causes the first magnetic particle 130c to be collected near the wall of an upstream region (i.e., a region more proximate to the first magnetic assembly 120c, up the direction of flow of blood from a downstream region more proximate to the second magnetic assembly 125c) of the blood vessel 110c proximate to the first magnetic assembly 120c (illustrated by the first path 135c of the first magnetic particle 130c). The second 140c and third 150c magnetic particles flow away from the first magnetic assembly 120c into the downstream region of the blood vessel 110c. The second magnetic assembly 125c exerting magnetic forces on the second 140c and third 150c magnetic particles causes the second magnetic particle 140c to be collected near the wall of the downstream region (i.e., a region more proximate to the second magnetic assembly 125c, down the direction of flow of blood from an upstream region more proximate to the first magnetic assembly 120c) of the blood vessel 110c proximate to the second magnetic assembly 125c (illustrated by the second path 145c of the second magnetic particle 140c). The third magnetic particle 150c flows away from the second magnetic assembly 125c and out of the illustrated portion of the blood vessel 110c (illustrated by the third path 155c of the third magnetic particle 150c).

The magnetic forces exerted by the magnetic assemblies 120c, 125c on first 130c, second 140c, and third 150c magnetic particles includes a force toward the wall of the blood vessel 110c to attract and/or collect the first 130c and second 140c magnetic particles. The magnetic force could additionally include a force parallel to the direction of the flow of blood in the blood vessel 110c, e.g., to slow the velocity of the first 130c and second 140c magnetic particles such that the first 130c and second 140c magnetic particles could be collected proximate to the first 120c and second 125c magnetic assemblies, respectively.

Note that additional or alternative magnetic assemblies could be applied to separate, collect, and/or otherwise manipulate additional magnetic particles and/or sets of magnetic particles. Magnetic particles could be separated according to one or more properties or combinations of properties of the magnetic particles (e.g., a characteristic size, a magnetic moment, a cross-sectional area, a drag coefficient, a state of binding and/or aggregation with one or more other particles or elements) and/or one or more properties of the environments of respective magnetic particles (e.g., a magnetic field intensity, a magnetic field gradient intensity, a magnetic field gradient direction, a fluid flow rate, a fluid viscosity, a fluid turbulence). In some examples, a magnetic device and/or magnetic assembly could be configured to separate a first set of magnetic particles having a characteristic size within a specified range of sizes from a second set of magnetic particles having characteristic sizes that are not within the specified range of sizes. For example, the first 130c, second 140c, and third 150c magnetic particles could have respective, decreasing characteristic sizes. In this example, the second magnetic particle 140c of FIG. 1C could be part of a first set of magnetic particles, and the first 130c and third 150c magnetic particles could be from a second set of magnetic particles, such that the magnetic device that includes the first 120c and second 125c magnetic assemblies could be described as separating first magnetic particles (i.e., the second magnetic particle 140c) having a characteristic size within a specified range of characteristic sizes from second magnetic particles (i.e., the first 130c and third 150c magnetic particles) having characteristic sizes outside the specified range. Other properties, ranges of properties, combinations of properties, or other specifying features of magnetic particles could be used to separate magnetic particles using magnetic devices having a variety of configurations.

It is also anticipated that magnetic particles could be separated in a continuous manner according to some continuously varying property or properties of the magnetic particles and/or the environment of the magnetic particles. For example, a magnetic assembly could be configured to separate and collect magnetic particles in blood such that magnetic particles having the largest characteristic size are collected in an upstream region, magnetic particles having the smallest characteristic size are collected in an downstream region, and magnetic particles having an intermediate characteristic size are collected in a region between the upstream and downstream regions that corresponds to the intermediate characteristic size.

Note that FIGS. 1A-1C illustrate separation of magnetic particles in the context of collecting one or more of the magnetic particles. It is also anticipated that separation of two or more magnetic particles and/or two or more sets of magnetic particles could be effected without collection of one or more of the magnetic particles. For example, a magnetic assembly could exert a magnetic force on first and second magnetic particles in a region of subsurface vasculature such that the first magnetic particles remain in the portion of subsurface vasculature for a longer period of time (e.g., by exerting a force to slow the first magnetic particles, by exerting a force to displace the first magnetic particles into a lower-flow region of the portion of subsurface vasculature). In an example, first magnetic particles could be displaced into a first region of a portion of subsurface vasculature (e.g., a medial location, a proximal location) and second magnetic particles could be displaced into a second region of a portion of subsurface vasculature (e.g., a lateral location, a distal location). Other types of separation of first and second magnetic particles that do not involve collection of magnetic particles are anticipated.

Other manipulations and/or magnetic forces could be applied to magnetic particles in an environment than those described above. The manipulations and/or magnetic forces could be related to properties of the magnetic particles (e.g., size, magnetic dipole moment, drag coefficient, cross-sectional area, degree of aggregation with other magnetic particles, whether the magnetic particles is bound to an analyte), properties of the environment containing the magnetic particles (e.g., a viscosity, a pH, a degree of polarity of a solvent, a flow rate, a flow profile, a degree of turbulence), or other factors.

Magnetic assemblies, devices containing magnetic assemblies, magnetic particles, and other aspects and embodiments described herein could be configured and/or operated to provide a variety of applications. In some examples, magnetic particles could be configured to bind to an analyte of interest, and a magnetic assembly could be configured to collect or otherwise manipulate the magnetic particles to enable the detection, extraction, modification, or other manipulation of the analyte. For example, a detector could be disposed proximate to a magnetic assembly that is configured to collect the magnetic particles, and the detector could detect one or more properties of the analyte bound to the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the collected magnetic particles sufficient to alter one or more properties of the analyte (e.g., to destroy, denature, heat, change a conformation state of, other otherwise modify the analyte). In some examples, collection of an analyte bound to magnetic particles by a magnetic assembly could enable the extraction of the analyte and magnetic particles (e.g., using a hypodermic needle).

The terms "binding", "bound", and related terms used herein are to be understood in their broadest sense to include any interaction between the receptor and the target or another functionalized particle such that the interaction allows the target to be modified or destroyed by energy emitted from a wearable device.

III. Example Wearable Magnetic Assemblies

In some applications, it can be desirable to produce magnetic fields having high magnitude, high magnitude of field gradient, a specified field profile, or other properties using a small device and using minimal power. For example, a wearable device, powered by a battery disposed in the device, could be configured to separate magnetic particles in the body of a wearer of a device. Such magnetic fields could be produced by magnetic assemblies that include permanent magnets, electromagnets, paramagnetic materials, flux-focusing and/or shielding shims or poles, or other elements.

A class of such magnetic assemblies includes unpowered elements, e.g., permanent magnets and other magnetic materials capable of generating a magnetic field having a desired profile, magnitude, or other property while requiring significantly no applied power. Such magnetic assemblies could include one or more permanent magnets, with each permanent magnet of the one or more permanent magnets having a respective magnetic moment that is oriented relative to an environment of interest (e.g., a portion of subsurface vasculature of a wearer of a device that includes the one or more permanent magnets) to enable some application (e.g., the exertion of a magnetic force to enable collection, separation, or some other manipulation of one or more magnetic particles in the portion of subsurface vasculature). Magnetic assemblies could additionally or alternatively include magnetic shims or poles (e.g., materials having high magnetic permeability or some other specified magnetic property) configured to focus magnetic flux toward a specified region of an environment and/or shield a specified region of an environment from magnetic flux.

Additionally or alternatively, magnetic flux could be produced by electromagnets or other powered elements. In embodiments described herein, a particular permanent magnet may be replaced with an electromagnet such that, when a specified current is applied to the electromagnet, the electromagnet could produce a pattern of magnetic flux substantially the same as a pattern of magnetic flux produced by the particular permanent magnet. In some examples the configuration of one or more magnetic elements (e.g., permanent magnets, magnetic shims, electromagnets) could be controlled by one or more actuators. For example, a permanent magnet could be mounted to an armature or other mechanism that is driven by an actuator (e.g., a servo) such that the actuator could be operated to rotate the permanent magnet and thus to rotate the direction of the magnetic moment of the magnet.

Figure 2A:
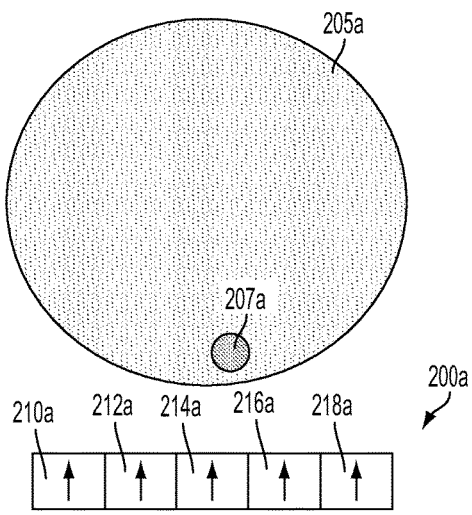
FIG. 2A is cross-sectional view of an example magnetic assembly, while positioned near a lumen of subsurface vasculature.

FIG. 2A illustrates a schematic diagram of an example magnetic assembly 200a comprising a plurality of permanent magnets 210a, 212a, 214a, 216a, 218a having respective magnetic moments (arrows). The magnetic assembly 200a is positioned proximate to a portion of subsurface vasculature 207a within a body of a human 205a. The magnetic assembly 200a could be part of a wearable device and the wearable device could further include a mount configured to mount the wearable device to an external body surface of the body of the human 205a proximate to the portion of subsurface vasculature 207a. The permanent magnets 210a, 212a, 214a, 216a, 218a of the magnetic assembly 200a can be configured to exert a magnetic force on magnetic particles (e.g., to separate first and second magnetic particles) in the portion of subsurface vasculature 207a.

Permanent magnets of a magnetic assembly could have magnetic moments oriented in substantially the same direction (as illustrated in the example of FIG. 2A) or could have a number of orientations relative to each other and/or to an environment of interest. In some examples, the orientations of the magnetic moments could be specified to increase one or more properties of a generated magnetic field (e.g., a field magnitude, a magnitude of a field gradient) in a first region and/or to reduce one or more properties of the generated magnetic field in a second region. For example, the magnetic moments of three or more magnets in a magnetic assembly could be arranged as a Halbach array to increase the magnitude of the magnetic field on one side of the magnetic assembly and to decrease the magnitude of the magnetic field on an opposite side of the magnetic assembly.

Figure 2B:
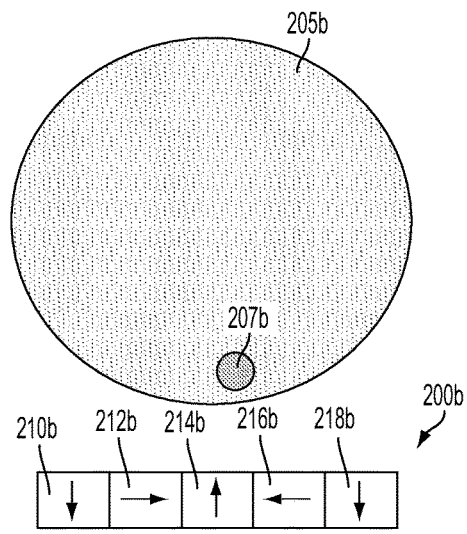
FIG. 2B is cross-sectional view of an example magnetic assembly, while positioned near a lumen of subsurface vasculature.

FIG. 2B illustrates a schematic diagram of an example magnetic assembly 200b comprising a plurality of permanent magnets 210b, 212b, 214b, 216b, 218b having respective magnetic moments (arrows) oriented such that the magnetic assembly forms a Halbach array. The magnetic assembly 200b is positioned proximate to a portion of subsurface vasculature 207b within a body of a human 205b. The magnetic assembly 200b could be part of a wearable device and the wearable device could further include a mount configured to mount the wearable device to an external body surface of the body of the human 205b proximate to the portion of subsurface vasculature 207b. The permanent magnets 210b, 212b, 214b, 216b, 218b of the magnetic assembly 200b can be configured to exert a magnetic force on magnetic particles (e.g., to separate first and second magnetic particles) in the portion of subsurface vasculature 207b. The permanent magnets 210b, 212b, 214b, 216b, 218b being arranged as a Halbach array comprises the orientation of the magnetic moment of an individual permanent magnet being substantially perpendicular to (i.e., rotated approximated ninety degrees relative to) the magnetic moments of permanent magnets in the array adjacent to the individual permanent magnet and substantially antiparallel to (i.e., rotated approximated 180 degrees relative to) permanent magnets in the array that are adjacent to the permanent magnets that are adjacent to the individual permanent magnet. Other arrangements of the magnetic moments of permanent magnets (or other flux-producing elements, e.g., electromagnets) of a magnetic array relative to the permanent magnets of the magnetic assembly and/or an environment of interest proximate to the magnetic assembly are anticipated.

In some examples, the magnetic assembly could wholly or partially enclose an environment (e.g., an aspect of a body of a wearer, e.g., a wrist). That is, a magnetic assembly and/or a wearable or other device including a magnetic assembly could have a concave surface configured to at least partially enclose a corresponding convex surface of an environment of interest (e.g., the magnetic assembly could have a concave surface configured to at least partially enclose a convex shape of an external body surface of a human or other wearer of the magnetic assembly). Further, one or more of a plurality of permanent magnets (or other flux-producing elements) of the magnetic assembly could be disposed on the concave surface of the magnetic assembly.

Figure 2C:
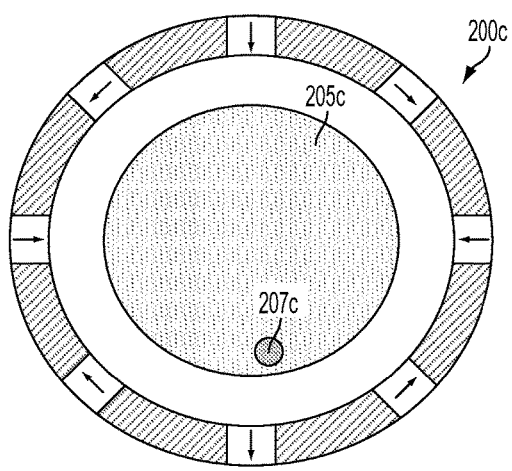
FIG. 2C is cross-sectional view of an example magnetic assembly, while positioned near a lumen of subsurface vasculature.
Figure 2D:
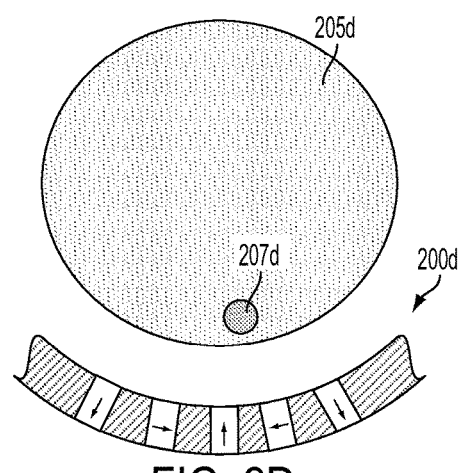
FIG. 2D is cross-sectional view of an example magnetic assembly, while positioned near a lumen of subsurface vasculature.

FIGS. 2C and 2D illustrate schematic diagrams of example magnetic assemblies 200c, 200d comprising respective pluralities of permanent magnets having respective magnetic moments (arrows) oriented such that the magnetic assemblies 200c, 200d form respective configurations of Halbach arrays. The magnetic assemblies 200c, 200d are positioned proximate to respective portions of subsurface vasculature 207c, 207d within respective bodies of respective humans 205c, 205d. The magnetic assemblies 200c could be part of respective wearable devices and the wearable devices could further include mounts configured to mount the wearable devices to respective external body surfaces of the bodies of the respective humans 205c, 205d proximate to the respective portions of subsurface vasculature 207c, 207d. The permanent magnets of the magnetic assemblies 200c, 200d can be configured to exert magnetic forces on magnetic particles (e.g., to separate first and second magnetic particles) in respective portions of subsurface vasculature 207c, 207d.

Magnetic assemblies can include magnetic poles (also called magnetic shims) configured to focus, block, or otherwise modify a pattern of magnetic flux and/or a magnetic field profile generated by one or more permanent magnets. The magnetic poles can have a variety of specified geometries and be composed of a variety of materials according to a variety of applications. The magnetic poles could be composed of materials having a specified magnetic property (e.g., permeability, reluctance, susceptibility, coercivity, remanence, saturation level). For example, the magnetic poles could be composed of one or more materials having a high magnetic permeability, e.g., mu-metal, iron, steel, metglas, Permalloy, ferrite, or other materials.

Figure 3A:
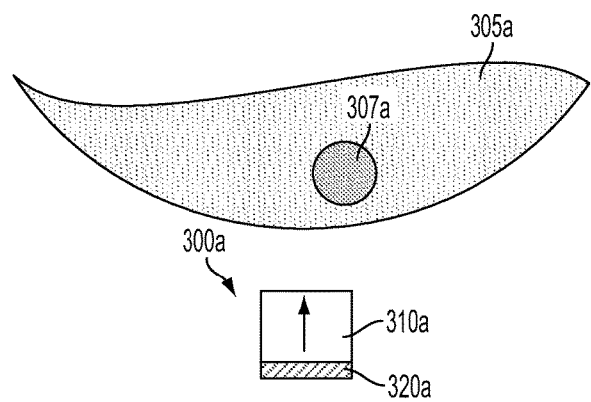
FIG. 3A is cross-sectional view of an example magnetic assembly, while positioned near a lumen of subsurface vasculature.

FIG. 3A illustrates a schematic diagram of an example magnetic assembly 300a comprising a permanent magnet 310a having a magnetic moment (arrow) and a magnetic pole 320a comprising a high-permeability material. The magnetic assembly 300a is positioned proximate to a portion of subsurface vasculature 307a within a body of a human 305a. The magnetic pole 320a comprises a layer of the high-permeability material disposed on a side of the magnetic assembly 300a opposite the human body 305a. The magnetic assembly 300a could be part of a wearable device and the wearable device could further include a mount configured to mount the wearable device to an external body surface of the body of the human 305a proximate to the portion of subsurface vasculature 307a. The permanent magnet 310a and pole 320a of the magnetic assembly 300a can be configured to exert a magnetic force on magnetic particles (e.g., to separate first and second magnetic particles) in the portion of subsurface vasculature 307a. Further, the magnetic pole 320a could act to increase a property (e.g., a magnitude, a gradient magnitude) of the magnetic field produced by the magnetic assembly 300a in the portion of subsurface vasculature 307a and/or to decrease a property (e.g., a magnitude, a gradient magnitude) of the magnetic field produced by the magnetic assembly 300a in a region away from the body of the human 305a (i.e., to 'shield' the region below the magnetic assembly 300a from the magnetic field produced by the permanent magnet 310a).

Figure 3B:
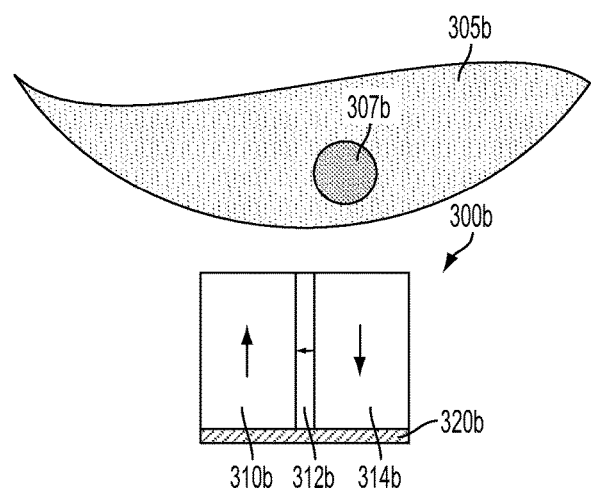
FIG. 3B is cross-sectional view of an example magnetic assembly, while positioned near a lumen of subsurface vasculature.

FIG. 3B illustrates a schematic diagram of an example magnetic assembly 300b comprising a plurality of permanent magnets 310b, 312b, 314b having respective magnetic moments (arrows) oriented such that the magnetic assembly forms a Halbach array. The magnetic assembly 300b additionally includes a magnetic pole 320a comprising a high-permeability material. The magnetic assembly 300b is positioned proximate to a portion of subsurface vasculature 307b within a body of a human 305b. The magnetic pole 320b comprises a layer of the high-permeability material disposed on a side of the magnetic assembly 300b opposite the human body 305b. The magnetic assembly 300b could be part of a wearable device and the wearable device could further include a mount configured to mount the wearable device to an external body surface of the body of the human 305b proximate to the portion of subsurface vasculature 307b. The permanent magnets 310b, 312b, 314b of the magnetic assembly 300b can be configured to exert a magnetic force on magnetic particles (e.g., to separate first and second magnetic particles) in the portion of subsurface vasculature 307b. The permanent magnets 310b, 312b, 314b being arranged as a Halbach array comprises the orientation of the magnetic moment of an individual permanent magnet being substantially perpendicular to (i.e., rotated approximated ninety degrees relative to) the magnetic moments of permanent magnets in the array adjacent to the individual permanent magnet and substantially antiparallel to (i.e., rotated approximated 180 degrees relative to) permanent magnets in the array that are adjacent to the permanent magnets that are adjacent to the individual permanent magnet. Other arrangements of the magnetic moments of permanent magnets of a magnetic array relative to the permanent magnets of the magnetic assembly and/or an environment of interest proximate to the magnetic assembly are anticipated. Further, the magnetic pole 320b could act to increase a property (e.g., a magnitude, a gradient magnitude) of the magnetic field produced by the magnetic assembly 300b in the portion of subsurface vasculature 307b and/or to decrease a property (e.g., a magnitude, a gradient magnitude) of the magnetic field produced by the magnetic assembly 300b in a region away from the body of the human 305b (i.e., to 'shield' the region below the magnetic assembly 300b from the magnetic field produced by the permanent magnets 310b, 312b, 314b).

Figure 3C:
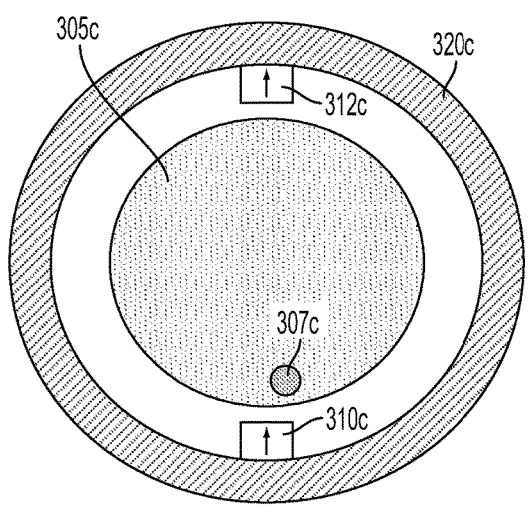
FIG. 3C is cross-sectional view of an example magnetic assembly, while positioned near a lumen of subsurface vasculature.

In some examples, the magnetic poles and/or permanent magnets of the magnetic assembly could wholly enclose an environment (e.g., a wrist or other body portion of a wearer). FIG. 3C illustrates a schematic diagram of an example magnetic assembly 300c comprising a plurality of permanent magnets (310c, 312c) having respective magnetic moments (arrows). The magnetic assembly 300c is positioned proximate to a portion of subsurface vasculature 307c within the body of a human 305c. The magnetic assembly 300c could be part of a wearable device and the wearable device could further include a mount configured to mount the wearable device to an external body surface of the body of the human 305c proximate to the portion of subsurface vasculature 307c. The magnetic assembly 300c wholly encloses a portion of the body of the human 307c with a magnetic pole 320c configured to transmit magnetic flux between the permanent magnets 310c, 312c to increase a property (e.g., a magnitude, a gradient magnitude) of the magnetic field produced by the magnetic assembly 300c in the portion of subsurface vasculature 307c and/or to decrease a property (e.g., a magnitude, a gradient magnitude) of the magnetic field produced by the magnetic assembly 300c outside of the enclosing magnetic pole 320c (i.e., to 'shield' the region outside of the enclosing magnetic pole 320c).

Figure 3D:
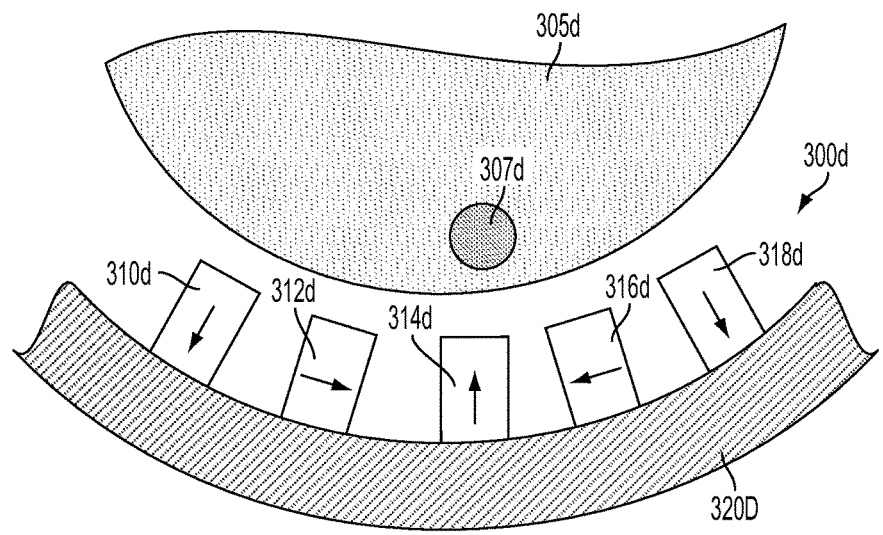
FIG. 3D is cross-sectional view of an example magnetic assembly, while positioned near a lumen of subsurface vasculature.

In some examples, the magnetic poles and/or permanent magnets of the magnetic assembly could partially enclose an environment (e.g., a wrist or other body portion of a wearer). FIG. 3D illustrates a schematic diagram of an example magnetic assembly 300d comprising a plurality of permanent magnets (310d, 312d, 314d, 316d, 318d) having respective magnetic moments (arrows). The magnetic assembly 300d is positioned proximate to a portion of subsurface vasculature 307d within a body of a human 305d. The magnetic assembly 300d could be part of a wearable device and the wearable device could further include a mount configured to mount the wearable device to an external body surface of the body of the human 305d proximate to the portion of subsurface vasculature 307d. The magnetic assembly 300d partially encloses a portion of the body of the human 307d with a magnetic pole 320d that is configured to increase a property (e.g., a magnitude, a gradient magnitude) of the magnetic field produced by the magnetic assembly 300d in the portion of subsurface vasculature 307d and/or to decrease a property (e.g., a magnitude, a gradient magnitude) of the magnetic field produced by the magnetic assembly 300d in a region away from the body of the human 305d (i.e., to 'shield' the region below the magnetic assembly 400d from the magnetic field produced by the permanent magnets 310d, 312d, 314d, 316d, 318d).

Figure 3E:
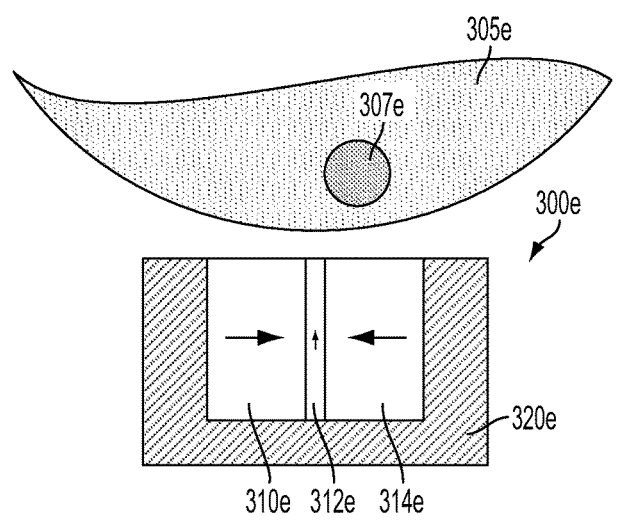
FIG. 3E is cross-sectional view of an example magnetic assembly, while positioned near a lumen of subsurface vasculature.

FIG. 3E illustrates a schematic diagram of an example magnetic assembly 300e comprising a plurality of permanent magnets 310e, 312e, 314e having respective magnetic moments (arrows) oriented such that the magnetic assembly forms a Halbach array, and such that a middle permanent magnet 312e has a magnetic moment oriented toward a portion of subsurface vasculature 307e within a body of a human 305e. The magnetic assembly 300e additionally includes a magnetic pole 320e comprising a high-permeability material. The magnetic assembly 300e is positioned proximate to the portion of subsurface vasculature 307e within the body of the human 305e. The magnetic pole 320e comprises a layer of the high-permeability material disposed on at least three sides of the magnetic assembly 300e: opposite the human body 305e, opposite the left permanent magnet 310e from the middle permanent magnet 312e, and opposite the right permanent magnet 314e from the middle permanent magnet 312e. The magnetic assembly 300e could be part of a wearable device and the wearable device could further include a mount configured to mount the wearable device to an external body surface of the body of the human 305e proximate to the portion of subsurface vasculature 307e. The permanent magnets 310e, 312e, 314e of the magnetic assembly 300e can be configured to exert a magnetic force on magnetic particles (e.g., to separate first and second magnetic particles) in the portion of subsurface vasculature 307e. The permanent magnets 310e, 312e, 314e being arranged as a Halbach array comprises the orientation of the magnetic moment of an individual permanent magnet being substantially perpendicular to (i.e., rotated approximated ninety degrees relative to) the magnetic moments of permanent magnets in the array adjacent to the individual permanent magnet and substantially antiparallel to (i.e., rotated approximated 180 degrees relative to) permanent magnets in the array that are adjacent to the permanent magnets that are adjacent to the individual permanent magnet. Other arrangements of the magnetic moments of permanent magnets of a magnetic array relative to the permanent magnets of the magnetic assembly and/or an environment of interest proximate to the magnetic assembly are anticipated. Further, the magnetic pole 320e could act to increase a property (e.g., a magnitude, a gradient magnitude) of the magnetic field produced by the magnetic assembly 300e in the portion of subsurface vasculature 307e and/or to decrease a property (e.g., a magnitude, a gradient magnitude) of the magnetic field produced by the magnetic assembly 300e in a region away from the body of the human 305e (i.e., to 'shield' the region below and/or to the sides of the magnetic assembly 300e from the magnetic field produced by the permanent magnets 310e, 312e, 314e).

In some embodiments, the magnetic assembly could have a narrowing geometry configured to concentrate a magnetic flux and/or to cause a magnetic field produced by the magnetic assembly to have a specified profile (i.e., a specified pattern of field magnitude, field direction, field gradient magnitude, field gradient direction) in one or more regions relative to the magnetic assembly. That is, an amount of flux and/or a magnitude of the magnetic field proximate to a narrow region of the narrowing geometry of the magnetic assembly (e.g., the 'top' peak of a truncated cone) could be greater than if the geometry did not narrow (e.g., the geometry was a cylinder, rather than a truncated cone). The narrowing geometry could include a magnetic pole and/or one or more permanent magnets. The narrowing geometry could be trapezoidal, conical, pyramidal, triangular, or some other narrowing geometry.

Figure 4A:
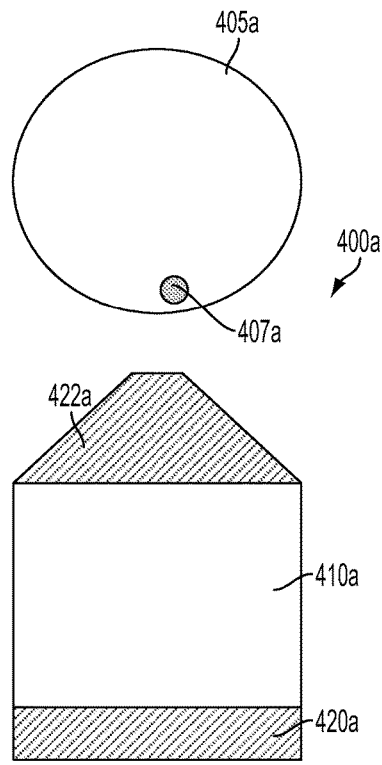
FIG. 4A is cross-sectional view of an example magnetic assembly, while positioned near a lumen of subsurface vasculature.

FIG. 4A illustrates a schematic diagram of an example magnetic assembly 400a comprising a magnetic flux source 410 and two magnetic poles 420a, 422a comprising a high-permeability material. The magnetic assembly 400a is positioned proximate to a portion of subsurface vasculature 407a within a body of a human 405a. The magnetic flux source 410a includes at least one permanent magnet, electromagnet or other magnetic flux-producing element. The magnetic flux source 410a can additionally include magnetic poles, air gaps, sensors, mechanically actuated elements (e.g., permanent magnets or other elements mounted to gears, gimbals, servos, or other actuators), or other components. In some examples, the magnetic flux source 510a could include a single permanent magnet having a magnetic moment oriented toward the portion of subsurface vasculature 407a. In some examples, the magnetic flux source 410a could include a plurality of permanent magnets having respective magnetic moments oriented to form a Halbach array. A first magnetic pole 420a comprises a layer of the high-permeability material disposed on a side of the magnetic assembly 400a opposite the human body 405a. A second (i.e., focusing) magnetic pole 422a comprises the high-permeability material disposed on a side of the magnetic assembly 400a toward the human body 405a. The second magnetic pole 422a could have one of a variety of narrowing geometries such that a first cross-sectional area of the second magnetic pole 422a proximate to the magnetic flux source 410a is greater than a second cross-sectional area of the second magnetic pole 422a farther from the magnetic flux source 410a (i.e., proximate to the human body 405a).

The magnetic assembly 400a could be part of a wearable device and the wearable device could further include a mount configured to mount the wearable device to an external body surface of the body of the human 405a proximate to the portion of subsurface vasculature 407a. The magnetic flux source 410a and magnetic poles 420a, 422a of the magnetic assembly 400a can be configured to exert a magnetic force on magnetic particles (e.g., to separate first and second magnetic particles) in the portion of subsurface vasculature 407a. Further, the magnetic poles 420a, 422a could act to increase a property (e.g., a magnitude, a gradient magnitude) of the magnetic field produced by the magnetic assembly 400a in the portion of subsurface vasculature 407a (e.g., proximate to a narrow end of the second magnetic pole 422a) and/or to decrease a property (e.g., a magnitude, a gradient magnitude) of the magnetic field produced by the magnetic assembly 400a in a region away from the body of the human 405a (i.e., to 'shield' the region below the magnetic assembly 400a from the magnetic field produced by the magnetic flux source 410a).

The second magnetic pole 422a could have a narrowing geometry chosen from a variety of narrowing geometries. The second magnetic pole 422a could be conical, pyramidal (e.g., a triangular pyramid, a square pyramid, a pyramid having some arbitrary polygonal base), a triangular prism, a partial ellipsoidal prism, a partial ellipsoid, or have some other narrowing or tapering geometry. The second magnetic pole 422a could have a truncated narrowing geometry (e.g., a truncated cone, a truncated pyramid, a trapezoidal prism). The second magnetic pole 422a could have a narrowing cross-sectional shape in a plane substantially perpendicular an external body surface of the human 405a proximate to which the magnetic assembly 400a is positioned. For example, the second magnetic pole 422a could have a triangular cross-section, a trapezoidal cross-section, a partial elliptical cross-section, or some other narrowing shape cross-section.

Elements (e.g., 410a, 420a, 422a) of the magnetic assembly 400a could have specified properties (e.g., sizes, thicknesses, widths, lengths, compositions, shapes) chosen so as to optimize certain properties of the magnetic assembly (e.g., a magnetic field magnitude, a magnetic field gradient magnitude) given one or more constraints on the magnetic assembly (e.g., a maximum volume, a maximum mass, a specified permanent magnet geometry). In some examples, the geometry of the second (focusing) magnetic pole 422a could be specified to maximize the magnetic field magnitude and the magnetic field gradient magnitude proximate to the second magnetic pole 422a for a given small size of magnetic flux source 410a (e.g., a small permanent (e.g., Nd52) magnet). For example, the second magnetic pole 422a could have a length of 5 millimeters, a width of 5 millimeters, a thickness of 2 millimeters, and could have a truncated pyramid geometry wherein the flat top of the truncated pyramid had a width of 1 millimeter. In some examples, the second magnetic pole 422a could have a size and/or geometry relative to other elements of the magnetic assembly 400a such that the second magnetic pole 422a is magnetically saturated. Other geometries and dimensions of elements of a magnetic assembly are anticipated.

Figure 4B:
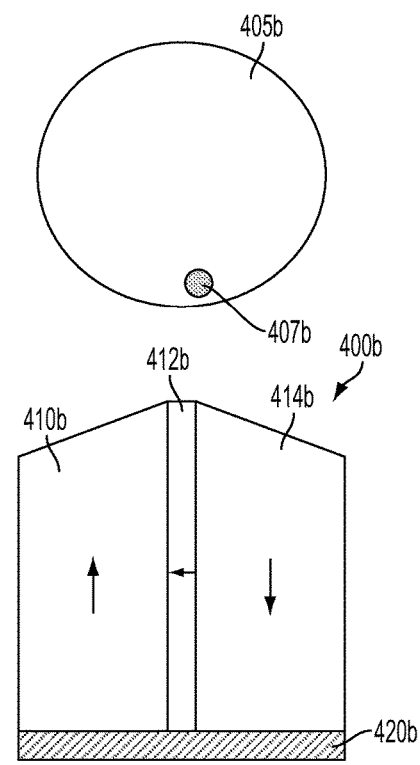
FIG. 4B is cross-sectional view of an example magnetic assembly, while positioned near a lumen of subsurface vasculature.

Additionally or alternatively, one or more permanent magnets of a magnetic assembly could have a narrowing geometry. FIG. 4B illustrates a schematic diagram of an example magnetic assembly 400b comprising a plurality of permanent magnets 410b, 412b, 414b having respective magnetic moments (arrows) that have, together, a narrowing geometry and whose magnetic moments are oriented such that the magnetic assembly forms a Halbach array. The magnetic assembly 400b additionally includes a magnetic pole 420a comprising a high-permeability material. The magnetic assembly 400b is positioned proximate to a portion of subsurface vasculature 407b within a body of a human 405b. The magnetic pole 420b comprises a layer of the high-permeability material disposed on a side of the magnetic assembly 400b opposite the human body 405b. The permanent magnets 410b, 412b, 414b could have one of a variety of narrowing geometries such that a cross-sectional shape of the permanent magnets 410b, 412b, 414b in a plane substantially perpendicular to an external body surface of the body of the human 405b proximate to the portion of subsurface vasculature 407b was narrower proximate to the external body surface.

The magnetic assembly 400b could be part of a wearable device and the wearable device could further include a mount configured to mount the wearable device to an external body surface of the body of the human 405b proximate to the portion of subsurface vasculature 407b. The permanent magnets 410b, 412b, 414b of the magnetic assembly 400b can be configured to exert a magnetic force on magnetic particles (e.g., to separate first and second magnetic particles) in the portion of subsurface vasculature 407b. The permanent magnets 410b, 412b, 414b being arranged as a Halbach array comprises the orientation of the magnetic moment of an individual permanent magnet being substantially perpendicular to (i.e., rotated approximated ninety degrees relative to) the magnetic moments of permanent magnets in the array adjacent to the individual permanent magnet and substantially antiparallel to (i.e., rotated approximated 180 degrees relative to) permanent magnets in the array that are adjacent to the permanent magnets that are adjacent to the individual permanent magnet. Other arrangements of the magnetic moments of permanent magnets of a magnetic array relative to the permanent magnets of the magnetic assembly and/or an environment of interest proximate to the magnetic assembly are anticipated. Further, the magnetic pole 420b could act to increase a property (e.g., a magnitude, a gradient magnitude) of the magnetic field produced by the magnetic assembly 400b in the portion of subsurface vasculature 407b and/or to decrease a property (e.g., a magnitude, a gradient magnitude) of the magnetic field produced by the magnetic assembly 400b in a region away from the body of the human 405b (i.e., to 'shield' the region below the magnetic assembly 400b from the magnetic field produced by the permanent magnets 410b, 412b, 414b).

The permanent magnets 410b, 412b, 414b could have a narrowing geometry chosen from a variety of narrowing geometries. The permanent magnets 410b, 412b, 414b could be conical, pyramidal (e.g., a triangular pyramid, a square pyramid, a pyramid having some arbitrary polygonal base), a triangular prism, a partial ellipsoidal prism, a partial ellipsoid, or have some other narrowing or tapering geometry. The permanent magnets 410b, 412b, 414b could have a truncated narrowing geometry (e.g., a truncated cone, a truncated pyramid, a trapezoidal prism). The permanent magnets 410b, 412b, 414b could have a narrowing cross-sectional shape in a plane substantially perpendicular an external body surface of the human 405b proximate to which the magnetic assembly 400b is positioned. For example, the permanent magnets 410b, 412b, 414b could have a triangular cross-section, a trapezoidal cross-section, a partial elliptical cross-section, or some other narrowing shape cross-section.

Figure 5:
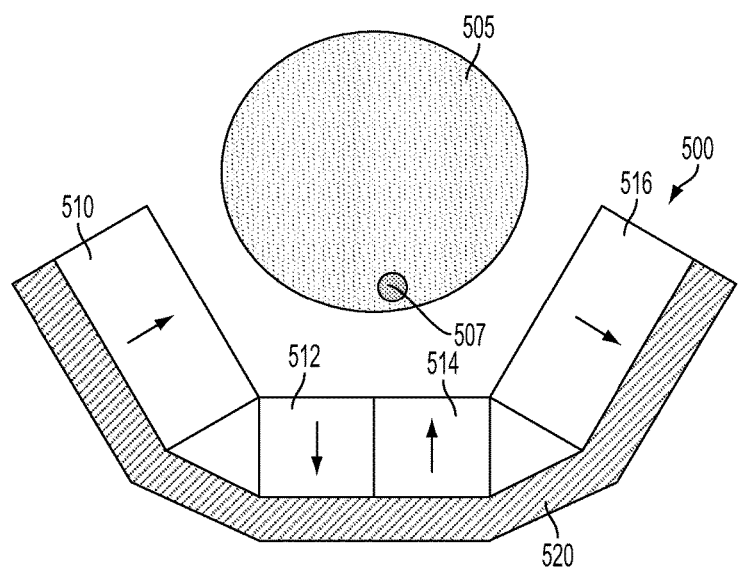
FIG. 5 is cross-sectional view of an example magnetic assembly, while positioned near a lumen of subsurface vasculature.

FIG. 5 illustrates a schematic diagram of an example magnetic assembly 500 comprising a magnetic pole 520 and a plurality of permanent magnets 510, 512, 514, 516 having respective magnetic moments (arrows). The magnetic assembly 500 is positioned proximate to a portion of subsurface vasculature 507 within a body of a human 505. The magnetic assembly 500 could be part of a wearable device and the wearable device could further include a mount configured to mount the wearable device to an external body surface of the body of the human 505 proximate to the portion of subsurface vasculature 507. The magnetic assembly 500 partially encloses a portion of the body of the human 507; that is, the permanent magnets 510, 512, 514, 516 are disposed on a concave surface of the magnetic device 500 and the concave surface is configured to partially enclose a convex surface (i.e., the external body surface) of the human 507. The magnetic pole 520 is configured to increase a property (e.g., a magnitude, a gradient magnitude) of the magnetic field produced by the magnetic assembly 500 in the portion of subsurface vasculature 507 and/or to decrease a property (e.g., a magnitude, a gradient magnitude) of the magnetic field produced by the magnetic assembly 500 in a region away from the body of the human 505 (i.e., to 'shield' the region below the magnetic assembly 500 from the magnetic field produced by the permanent magnets 510, 512, 514, 516). First 510 and third 514 permanent magnets have magnetic moments pointing into respective proximate regions of the external body surface of the human 505 and third 512 and fourth 516 permanent magnets have magnetic moments pointing away from respective proximate regions of the external body surface of the human 505.

Magnetic assemblies, devices containing magnetic assemblies, magnetic particles, and other aspects and embodiments described herein (e.g., 200a, 200b, 200c, 200d, 300a, 300b, 300c, 300d, 300e, 400a, 400b, 500) could be configured and/or operated to provide a variety of applications. In some examples, magnetic particles could be configured to bind to an analyte of interest, and a magnetic assembly could be configured to collect or otherwise manipulate the magnetic particles to enable the detection, extraction, modification, or other manipulation of the analyte. For example, the magnetic assembly could be configured to produce a magnetic field in the portion of subsurface vasculature such that first magnetic particles (i.e., aggregate particles comprising instances of an analyte and magnetic particles bound thereto) experience a greater magnetic force than second magnetic particles (i.e., unbound instances of the magnetic particles) such that the first and second magnetic particles could be separated.

In some examples, the magnetic assembly could be configured to exert a first magnetic force on first magnetic particles and to exert a second magnetic force on second magnetic particles such that the difference between the first and second magnetic forces is sufficient to cause separation of the first and second magnetic particles. For example, the first magnetic particles could have a first magnetic moment and the second magnetic particles could have a second magnetic moment that is different from the first magnetic moment. Additionally or alternatively, the magnetic force exerted on the magnetic particles particles could be substantially the same between different set of magnetic particles (e.g., between first and second magnetic particles), but some other force (e.g., fluid drag) could be different between first and second magnetic particles such that exerting the magnetic force causes separation of the first and second magnetic particles.

In some examples, the magnetic or other differences in properties between first and second sets of magnetic particles could be intrinsic to individual instances of the first and second magnetic particles. For example, the first magnetic particles could have a first magnetic moment, coefficient of drag, cross-sectional area, or some other property, and the second magnetic particles could have a second magnetic moment, coefficient of drag, cross-sectional area, or some other property such that the first and second magnetic particles can be separated by a magnetic assembly.

In some examples, the magnetic or other differences in properties between first and second sets of magnetic particles could be related to the environment of the first and second magnetic particles. For example, the first magnetic particles could be aggregate particles consisting of multiple instances of second magnetic particles and/or other elements (e.g., multiple instances of the second magnetic particles bound to a cell or other analyte). For example, blood within the portion of subsurface vasculature containing the magnetic particles could exhibit a flow profile, and the first magnetic particles could be located in a low-flow region of the flow profile and the second magnetic particles could be located in a high-flow region of the flow profile such that the magnetic forces exerted by the magnetic assembly cause separation of the first and second magnetic particles (e.g., collection of the first magnetic particles in the portion of subsurface vasculature, while the second magnetic particles flow away from the portion of subsurface vasculature.

In some embodiments, a detector could be disposed proximate to a magnetic assembly that is configured to separate the magnetic particles, and the detector could detect one or more properties of an analyte bound to some or all of the magnetic particles (e.g., by detecting an optical property of the analyte and/or magnetic particles (e.g., fluorescent detection of a fluorophore), by detecting a magnetic property of the magnetic particles). Additionally or alternatively, an energy emitter could be disposed proximate to the magnetic assembly, and the energy emitter could emit energy toward the separated and/or collected magnetic particles sufficient to alter one or more properties of the analyte (e.g., to destroy, denature, heat, change a conformation state of, other otherwise modify the analyte). In some examples, separation and collection of an analyte bound to magnetic particles by a magnetic assembly could enable the extraction of the analyte and magnetic particles (e.g., using a hypodermic needle).

In some applications, separation or other manipulation of magnetic particles could enable detection and/or modification of an analyte. For example, the reaction (e.g., a differential and/or absolute motion) of a magnetic particle to a magnetic field generated by a magnetic assembly (e.g., 200a, 200b, 200c, 200d, 300a, 300b, 300c, 300d, 300e, 400a, 400b, 500) could be detected, and one or more properties of the reaction could be used to determine one or more properties of the magnetic particle. For example, the degree of change in velocity of a magnetic particle, when exposed to the magnetic field of the magnetic assembly, could be related to whether the magnetic particle was bound to an analyte. In some examples, the magnetic particles could be configured to couple an oscillating electromagnetic field into an increase in heat proximate to the magnetic particle, and this increase in heat could be used to detect one or more properties of the magnetic particle and/or to modify the environment proximate to the particle (e.g., to denature an analyte bound to the magnetic particle). Other configurations, operations, and applications of the embodiments described herein are anticipated.

Figure 6:
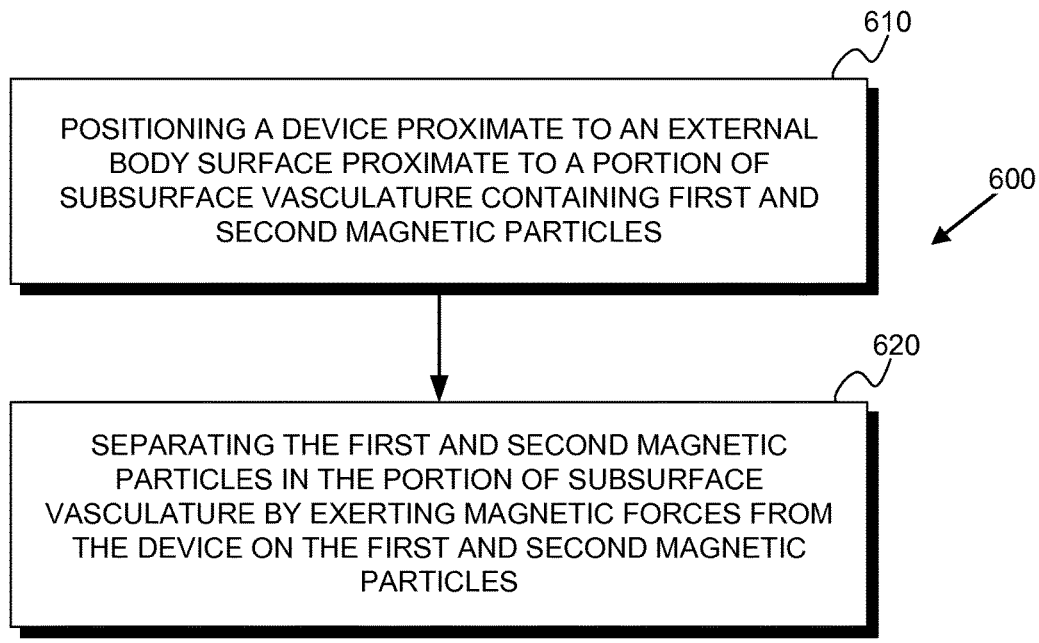
FIG. 6 is a flowchart of an example method.

IV. Illustrative Methods for Using a Magnetic Assembly to Exert Forces on Magnetic Particles FIG. 6 is a flowchart of an example method 600 for exerting a separating magnetic force on magnetic particles using a wearable device. The method 600 includes positioning the wearable device proximate to an external surface proximate to a portion of subsurface vasculature containing first and second magnetic particles 610. This could include operating a mount included in the wearable device that is configured to enclose a portion of the body of the wearer (e.g., a wrist, an ankle, a chest) to secure the wearable device at a specified location relative to the portion of subsurface vasculature. In some examples, this could include positioning the magnetic device relative to a visible or other landmark on or beneath the external body surface (e.g., a tattoo, a visible artery or vein, bony protuberance, a joint, a birth mark). In some examples, this could include manipulating and/or changing the location of the wearable device relative to some indication from the device, e.g., and indication from the wearable device that the magnetic assembly was located proximate to the portion of subsurface vasculature.

The method 600 additionally includes separating the first and second magnetic particles in the portion of subsurface vasculature by exerting magnetic forces from the device on the first and second magnetic particles 620. This could include exerting an attractive force on the magnetic particles sufficient to collect the first and/or second magnetic particles in the portion of subsurface vasculature. This could include exerting a magnetic force having a direction substantially parallel to a direction of blood flow in the portion of subsurface vasculature. This could include exerting a magnetic force having a direction substantially toward a wall of the portion of subsurface vasculature. Other examples of exerting a magnetic force on magnetic particles using the wearable device and applications thereof as described herein and otherwise are anticipated.

The method 600 could include additional steps or elements. For example, the method 600 could include introducing the first and second magnetic particles into the portion of subsurface vasculature (e.g., injecting, ingesting, transdermally transferring, or otherwise introducing the engineered particles into a lumen of vasculature of a human). In some examples, the magnetic particles could be configured to bind to an analyte and to enable detection of one or more properties of, modification of one or more properties of, and/or some other interaction with the analyte.

In some examples, the method 600 could include detecting one or more properties of an analyte to which the first and/or second magnetic particles are configured to bind. This could include operating a detector of the wearable device to detect the one or more properties of the bound analyte. In some examples, this could include exerting an attractive magnetic force on the first and/or second magnetic particles such that the first and/or second magnetic particles and instances of the analyte bound thereto are caused to collect in a portion of subsurface vasculature proximate to the magnetic assembly and/or the detector of the wearable device. In some examples, this could include exerting a first magnetic force on first magnetic particles that are bound to the analyte and exerting a second magnetic force on second magnetic particles that are not bound to the analyte such that the first and second magnetic particles are separated such that a detector of the wearable device substantially only detects one or more properties of the first set of magnetic particles. Other methods of detecting one or more properties of an analyte using a magnetic assembly disposed in a wearable device positioned proximate to a portion of subsurface vasculature are anticipated.

In some examples, the wearable device could include an electromagnet configured to exert the magnetic force on the first and second magnetic particles. The method 600 could further include operating the electromagnet to exert the magnetic force. This could include applying a specified current and/or voltage to one or more windings of the electromagnet. This could include applying a first specified current and/or voltage to one or more windings of the electromagnet during a first period of time and a second specified current and/or voltage to one or more windings of the electromagnet during a first period of time. This could include applying a current and/or voltage to one or more windings of the electromagnet according to a detected property of the wearable device, the portion of subsurface vasculature, the first and/or second magnetic particles, and/or an analyte or other element in blood in the portion of subsurface vasculature. For example, an amount of the first magnetic particles in the portion of subsurface vasculature could be detected, and a current applied to a winding of the electromagnet could be increased or decreased according to the detected amount such that the amount of the first magnetic particles in the portion of subsurface vasculature is substantially equal to a specified amount.

In some examples, the method 600 could include extracting the first magnetic particles from the portion of subsurface vasculature. For example, a hypodermic needle could be inserted into the portion of subsurface vasculature and a plunger or other element of the hypodermic needle could be operated to extract the blood containing the first magnetic particles from the portion of subsurface vasculature. In another example, the end of a catheter or some other temporarily or semi-permanently placed tube could be disposed in the portion of subsurface vasculature such that the first magnetic particles could be extracted continuously, over a period of time. The second magnetic particles and/or some other magnetic particle or other components of the blood could additionally or alternatively be extracted from the portion of subsurface vasculature.

V. Example Wearable Devices

Figure 7:
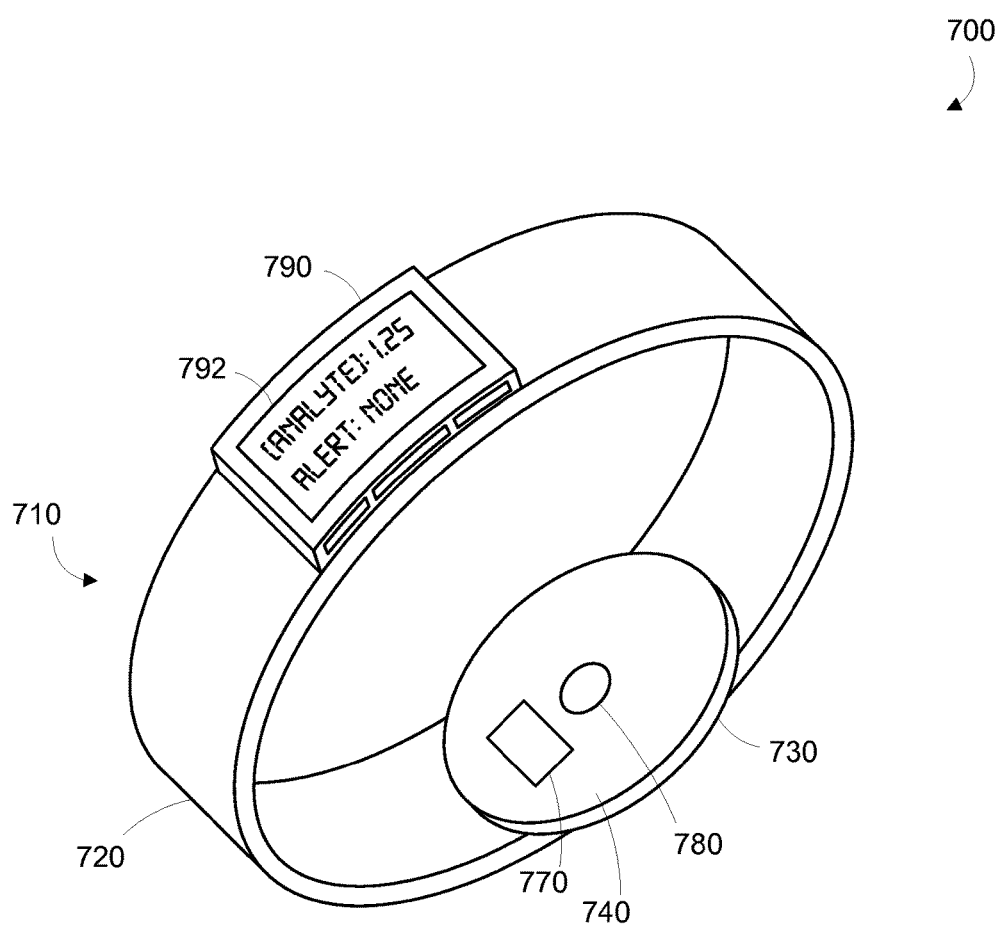
FIG. 7 is a perspective view of an example wearable device.

A wearable device 700 can measure a plurality of physiological parameters of a person wearing the device, among other functions. Some or all of the functions of the wearable device 700 are enabled by separation of magnetic particles in blood of the wearer of the device. Such separation can be effected by the exertion of magnetic forces on the magnetic particles by a magnetic assembly (e.g., 120a, 120b, 120c, 200a, 200b, 200c, 200d, 300a, 300b, 300c, 300d, 300e, 400a, 400b, 500) disposed on or in the wearable device 700. The term "wearable device," as used in this disclosure, refers to any device that is capable of being worn at, on or in proximity to a body surface, such as a wrist, ankle, waist, chest, or other body part. In order to separate magnetic particles and/or take in vivo measurements in a non-invasive manner from outside of the body, the wearable device may be positioned on a portion of the body where subsurface vasculature containing magnetic particles is easily affectable (e.g., by exertion of magnetic forces) and observable, depending on the type of modification and detection systems used. The device may be placed in close proximity to the skin or tissue, but need not be touching or in intimate contact therewith. A mount 710, such as a belt, wristband, ankle band, etc. can be provided to position the device at, on or in proximity to the body surface. The mount 710 may prevent the wearable device 700 from moving relative to the body to ensure effective separation of magnetic particles and/or detection of one or more physiological properties of the wearer. In one example, shown in FIG. 7, the mount 710, may take the form of a strap or band 720 that can be worn around a part of the body. Further, the mount 710 may include an adhesive material for adhering the wearable device 700 to the body of a wearer.

A separation platform 730 is disposed on the mount 710 such that it can be positioned on the body where subsurface vasculature is easily affected. An inner face 740 of the modification platform is intended to be positioned facing to the body surface. The separation platform 730 may house a magnetic assembly 780. In such embodiments, the magnetic assembly 780 could be configured to separate magnetic particles in a portion of subsurface vasculature by exerting magnetic forces on the magnetic particles. Separation of the magnetic particles could take the form of one or more of the varieties of separation described herein (e.g., in combination with FIGS. 1A-C). The magnetic assembly 780 could additionally act to collect magnetic particles in the portion of subsurface vasculature. The magnetic assembly 780 could include electromagnets, permanent magnets, magnetic shims, or other magnetic material configured in a variety of ways (e.g., configured similarly to magnetic assemblies 200a, 200b, 200c, 200d, 300a, 300b, 300c, 300d, 300e, 400a, 400b, 500).

In some examples, the wearable device 700 further includes at least one detector 770 for detecting at least one physiological parameter, which could include any parameters that may relate to the health of the person wearing the wearable device. For example, the detector 770 could be configured to measure blood pressure, pulse rate, respiration rate, skin temperature, etc. At least one of the detectors 770 could be configured to non-invasively measure one or more properties of magnetic particles in blood and/or analytes bound thereto circulating in subsurface vasculature proximate to the wearable device. In a non-exhaustive list, detector 770 may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., RF, magnetic resonance) sensor. Operation of the detector 770 could be related to and/or contingent on separation of magnetic particles by the magnetic assembly 780.

The wearable device 700 may also include a user interface 790 via which the wearer of the device may receive one or more recommendations or alerts generated from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 790 may include a display 792 where a visual indication of the alert or recommendation may be displayed. The display 792 may further be configured to provide an indication the battery status of the device or the status of the modification system or an indication of any measured physiological parameters, for instance, the concentrations of certain blood analytes being measured.

Figure 8A:
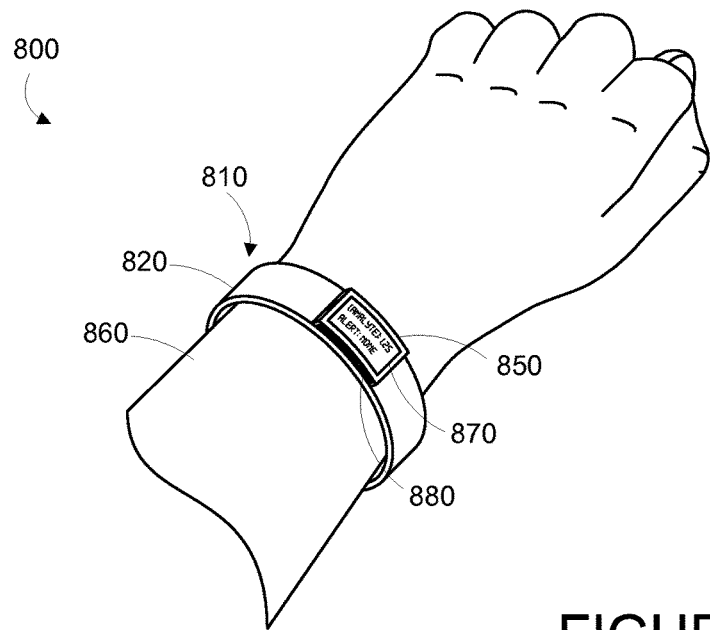
FIG. 8A is a perspective top view of an example wrist-mounted device, when mounted on a wearer's wrist.
Figure 8B:
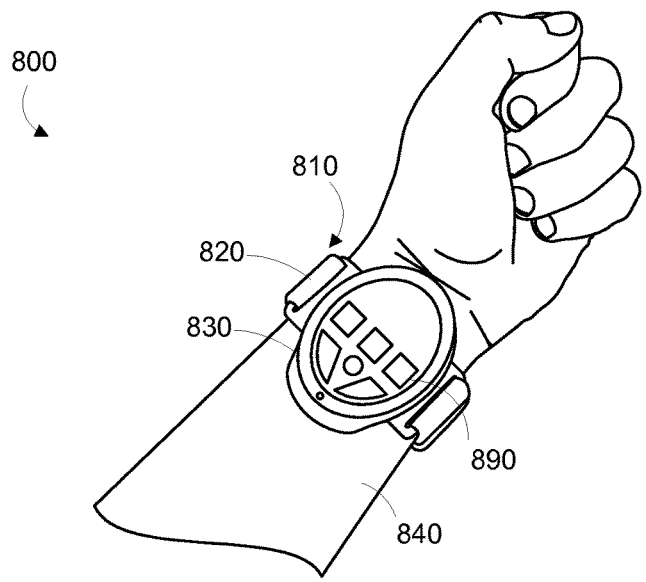
FIG. 8B is a perspective bottom view of an example wrist-mounted device shown in FIG. 8A, when mounted on a wearer's wrist.

In one example, the wearable device is provided as a wrist-mounted device, as shown in FIGS. 8A and 8B. The wrist-mounted device may be mounted to the wrist of a living subject with a wristband or cuff, similar to a watch or bracelet. As shown in FIGS. 8A and 8B, the wrist mounted device 800 may include a mount 810 in the form of a wristband 820, a separation platform 830 positioned on the anterior side 840 of the wearer's wrist, and a user interface 850 positioned on the posterior side 860 of the wearer's wrist. The wearer of the device may receive, via the user interface 850, one or more recommendations or alerts generated either from a remote server or other remote computing device, or alerts based on physiological properties of a wearer detected by the wrist-mounted device 800. Such a configuration may be perceived as natural for the wearer of the device in that it is common for the posterior side 860 of the wrist to be observed, such as the act of checking a wrist-watch. Accordingly, the wearer may easily view a display 870 on the user interface. Further, the separation platform 830 may be located on the anterior side 840 of the wearer's wrist where the subsurface vasculature may be readily affectable. However, other configurations are contemplated.

The display 870 may be configured to display a visual indication of the alert or recommendation and/or an indication of the status of the wearable device and an indication of measured physiological parameters, for instance, the concentrations of certain target blood analytes bound to separated magnetic particles in the blood. Further, the user interface 850 may include one or more buttons 880 for accepting inputs from the wearer. For example, the buttons 880 may be configured to change the text or other information visible on the display 870. As shown in FIG. 8B, separation platform 830 may also include one or more buttons 890 for accepting inputs from the wearer. The buttons 890 may be configured to accept inputs for controlling aspects of the wrist-mounted device 800, such as inputs indicating the wearer's current health state (i.e., normal, migraine, shortness of breath, heart attack, fever, "flu-like" symptoms, food poisoning, etc.).

CONCLUSION

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

While various aspects and embodiments herein are described in connection with exerting forces on magnetic particles disposed in a portion of subsurface vasculature, other applications and environments are possible. Aspects and embodiments herein could be applied to exert forces on magnetic particles in in vivo or in vitro human or animal tissues, a fluid in a scientific, medical, or industrial testing process, or some other environment. Magnetic forces could be exerted on magnetic particles disposed in a natural environment, e.g., a lake, river, stream, marsh, or other natural locale. Magnetic forces could be exerted on magnetic particles disposed in a fluid environment of an industrial process or other artificial environment, e.g., a water treatment process, a food preparation process, a pharmaceutical synthesis process, a chemical synthesis process, a brewing and/or distilling process, or other artificial locale. Magnetic forces could be exerted on magnetic particles disposed in an environment that includes a flowing fluid (e.g., fluid flowing in a blood vessel, a pipe, a culvert) and/or a static fluid. Other environments and applications of aspects and embodiments described herein are anticipated.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. A method, comprising:
    positioning a device proximate to an external body surface that is proximate to a portion of subsurface vasculature, wherein the portion of subsurface vasculature contains first magnetic particles and second magnetic particles, wherein the first and second magnetic particles selectively bind with one or more analytes of interest;
    separating the first and second magnetic particles in the portion of subsurface vasculature, wherein separating the first and second magnetic particles comprises exerting magnetic forces on the first and second magnetic particles, wherein the magnetic forces are exerted by the device; and
    detecting, using a detector, one or more properties of the one or more analytes of interest based on one or more properties of the separated first and/or second magnetic particles and/or the one or more analytes bound thereto.

2. The method of claim 1, further comprising introducing the first and second magnetic particles into the portion of subsurface vasculature.

3. The method of claim 1, wherein the device comprises at least one electromagnet, wherein separating the first and second magnetic particles in the portion of subsurface vasculature comprises operating at least one electromagnet of the device to exert the magnetic forces on the first and second magnetic particles, respectively.

4. The method of claim 1, wherein the device comprises at least one permanent magnet, wherein the magnetic forces are caused by at least one permanent magnet of the device.

5. The method of claim 1, wherein the magnetic forces include forces parallel to a direction of flow of blood in the portion of subsurface vasculature.

6. The method of claim 1, wherein the magnetic forces include forces toward a wall of the portion of subsurface vasculature.

7. The method of claim 1, further comprising:
    extracting the first magnetic particles from the portion of subsurface vasculature.

8. The method of claim 1, wherein separating the first and second magnetic particles in the portion of subsurface vasculature comprises collecting the first magnetic particles in the portion of subsurface vasculature while allowing the second magnetic particles to flow away from the portion of subsurface vasculature.

9. The method of claim 1, wherein separating the first and second magnetic particles in the portion of subsurface vasculature comprises:
    collecting, in an upstream region of the portion of subsurface vasculature, the first magnetic particles while allowing the second magnetic particles to flow away from the upstream region to a downstream region of the portion of subsurface vasculature; and
    collecting, in the downstream region of the portion of subsurface vasculature, the second magnetic particles.

10. The method of claim 1, wherein the first magnetic particles are bound to the one or more analytes of interest and the second magnetic particles are not bound to the one or more analytes of interest.

11. The method of claim 1, wherein the first magnetic particles selectively interact with a first analyte of interest, and wherein the second magnetic particles selectively interact with a second analyte of interest.

12. The method of claim 1, wherein the first magnetic particles have a first characteristic size, wherein the second magnetic particles have a second characteristic size different than the first characteristic size, and wherein separating the first and second magnetic particles in the portion of subsurface vasculature comprises collecting magnetic particles in the subsurface vasculature having characteristic sizes within a specified range of sizes, wherein the specified range of sizes includes the first characteristic size and does not include the second characteristic size.

13. An apparatus, comprising:
   a magnetic field producer, wherein the magnetic field producer comprises at least one permanent magnet and/or at least one electromagnet that, when positioned proximate to an external body surface that is proximate to a portion of subsurface vasculature containing first magnetic particles and second magnetic particles, wherein the first and second magnetic particles selectively bind with one or more analytes of interest, the magnetic field producer exerts magnetic forces on the first and second magnetic particles sufficient to separate the first and second magnetic particles in the portion of subsurface vasculature; and
   a detector, wherein the detector is configured to detect one or more properties of the one or more analytes of interest based on one or more properties of the separated first and/or second magnetic particles and/or the one or more analytes bound thereto.

14. The apparatus of claim 13, wherein the apparatus further comprises:
   a mount that can mount the apparatus to the external body surface such that the magnetic field producer exerts the magnetic forces on the first and second magnetic particles in the portion of subsurface vasculature.

15. The apparatus of claim 13, wherein the magnetic field producer comprises at least one permanent magnet.

16. The apparatus of claim 13, wherein the magnetic forces exerted by the magnetic field producer are sufficient to collect the first magnetic particles in a first region of the portion of subsurface vasculature while allowing the second magnetic particles to flow away from the first region of the portion of subsurface vasculature.

* * * * *